United States Patent [19]
Pursley et al.

[11] Patent Number: 5,156,605
[45] Date of Patent: * Oct. 20, 1992

[54] AUTOMATIC INTERNAL COMPRESSION-DISTRACTION-METHOD AND APPARATUS

[75] Inventors: John A. Pursley; Jordon M. Holloway, both of Indian; Thomas L. Wakefield, Anchorage, all of Ak.

[73] Assignee: Autogenesis Corporation, Anchorage, Ak.

[*] Notice: The portion of the term of this patent subsequent to Nov. 27, 2007 has been disclaimed.

[21] Appl. No.: 713,483

[22] Filed: Jun. 11, 1991

Related U.S. Application Data

[63] Continuation-in-part of Ser. No. 548,814, Jul. 6, 1990.

[51] Int. Cl.$^5$ ............................................. A61B 17/56
[52] U.S. Cl. ................................... 606/54; 606/56; 606/58; 606/59
[58] Field of Search ..................................... 606/53–59

[56] References Cited

U.S. PATENT DOCUMENTS

| | | | |
|---|---|---|---|
| 3,941,123 | 3/1976 | Volkov | 606/55 |
| 3,976,060 | 8/1976 | Hildebrandt | 606/58 |
| 3,977,397 | 8/1976 | Kalnberz | 606/56 |
| 3,985,127 | 10/1976 | Volkov | 606/55 |
| 4,033,340 | 7/1977 | Kalnberz | 606/56 |
| 4,338,927 | 7/1982 | Volkov | 606/55 |
| 4,570,625 | 2/1986 | Harris | 606/58 |
| 4,615,338 | 10/1986 | Ilizarov | 606/58 |
| 4,768,524 | 9/1988 | Hardy | 606/54 |
| 4,784,125 | 11/1988 | Monticelli | 606/56 |
| 4,923,458 | 5/1990 | Fischer | 606/57 |
| 4,973,331 | 11/1990 | Pursley | 606/56 |

FOREIGN PATENT DOCUMENTS

| | | |
|---|---|---|
| 2417233 | 10/1975 | Fed. Rep. of Germany . |
| 2705154 | 2/1977 | Fed. Rep. of Germany . |
| 2601938 | 7/1977 | Fed. Rep. of Germany . |
| 2845647 | 5/1980 | Fed. Rep. of Germany . |
| 3722595 | 1/1989 | Fed. Rep. of Germany . |
| 2628627 | 9/1989 | France . |
| WO89/11255 | 11/1989 | PCT Int'l Appl. . |
| 1651779 | 2/1983 | U.S.S.R. . |
| 1122308 | 11/1984 | U.S.S.R. . |
| 1560173 | 4/1990 | U.S.S.R. . |

OTHER PUBLICATIONS

Soviet Inventions, Illustrated, week 8519. Jun. 19, 1985, section P/Q, class P31, abstract No. 85-115442/19, Derwent Publications Ltd., London GB and SU 1122308, Kurgan Orthopaedics, 1984.

"Operative Lengthening of the Femur Using a Completely Implantable Distractor Apparatus" by A. N. Witt and M. Jager, Arch. of Orthop. and Traumat. Surg. 92, 291–296 (1978), (English translation provided).

(List continued on next page.)

Primary Examiner—Michael A. Brown
Attorney, Agent, or Firm—Dickstein, Shapiro & Morin

[57] ABSTRACT

An orthopaedic system is provided which includes a plurality of support members, a plurality of rods interconnecting the support members, a plurality of pins attached to the support members for passing through bone of a patient, and an automatic drive mechanism to control an adjustment mechanism of the rods to adjust the rod length of the rods to alter the relative positions of the support members. The drive mechanism includes at least one motor for incrementally adjusting the adjustment mechanism of at least one of the rods and a controller mechanism for providing pulses to the motor and for storing information regarding the number of stepwise adjustments of the rod length by the motor. An internal orthopaedic system is also disclosed in which a telescoping rod driven by an internal drive screw is placed internal to the bone of a patient and driven by means of either a flexible drive shaft connected to a motor and controller assembly or an internal motor and controller assembly.

24 Claims, 26 Drawing Sheets

OTHER PUBLICATIONS

"Results of Animal Experiments with a Fully Implantable Distractor Apparatus for Operative Leg Lengthening" by A. N. Witt, M. Jager, H. Bruns, E. Kusswetter, J. J. Hildebrandt, R. Cramer and A. Vogel, Arch. of Orthop. and Traumat. Surg. 88, 273-279 (1977), (English translation provided).

"Development of a Fully Implantable Distractor-Device for Operative Leg-Lengthening", 6th International Symposium on External Control of Human Extremities in Dubrovnik, Yugoslavia Hildebrandt, J. J., Cramer, R., Yager, M., Vogel, A. (1978).

Vollinplantierbaren Distraktions-gerat fur die operative Beinverlangerung, Teil I: Konstruktion und Anwendung im Tierversuch, J. J. Hildebrandt, R. Cramer, A. Vogel, M. Jager, H. Bruns, H. Stritzinger, Fachtagungen Medex, Basel/Schweiz (1976), Biomed. Techn., Band 21, 259-260, Erganzungsband Jun. 1976. Operative Beinverlangerungmiteinem Vollinplantierbaren Distraktionsgerat by J. J. Hildebrandt, M. Jager and A. N. Witt.

"Continous Femur Lengthening with Intramedullary Stabilization", J. Gotz and W. D. Schellman, Arch. of Orthop. and Traumat. Surg. 82, 305-310 (1975), (English translation provided).

"The Extension Pin, A new Way of Lengthening the Femur and Tibia" by F. Baumann and J. Harms, Arch. of Orthop. and Traumat. Surg. 90, 139-146 (1977), (English translation provided).

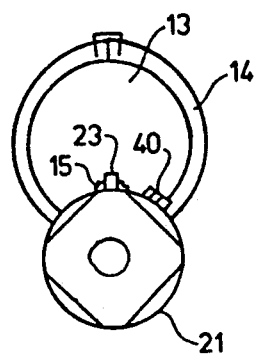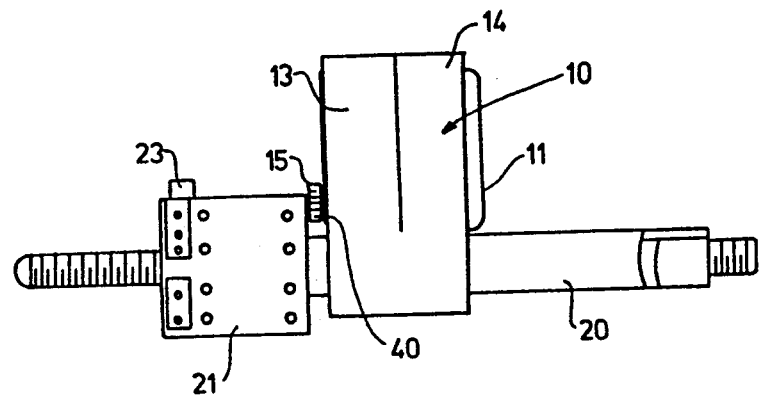
FIG. 1b  FIG. 1a
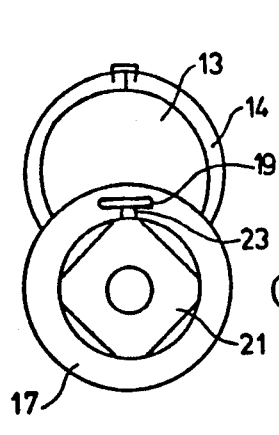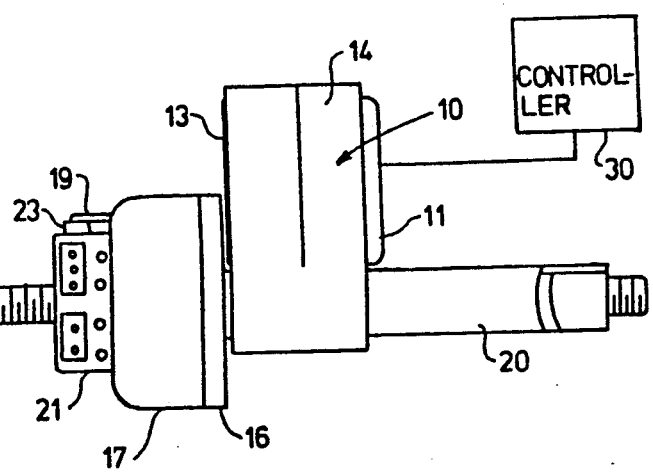
FIG. 1d  FIG. 1c

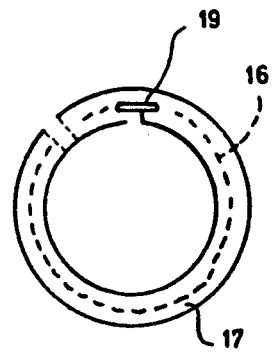
FIG. 2
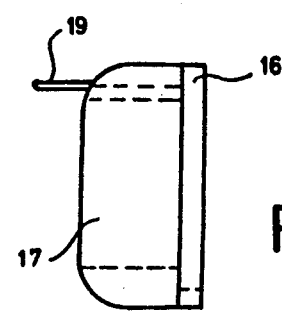
FIG. 3
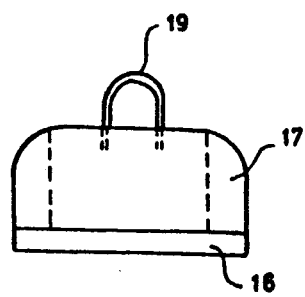
FIG. 4
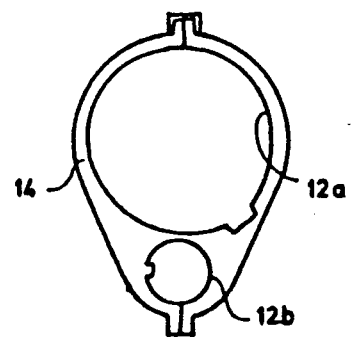
FIG. 5
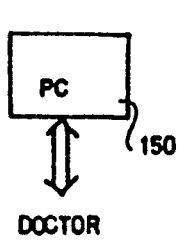
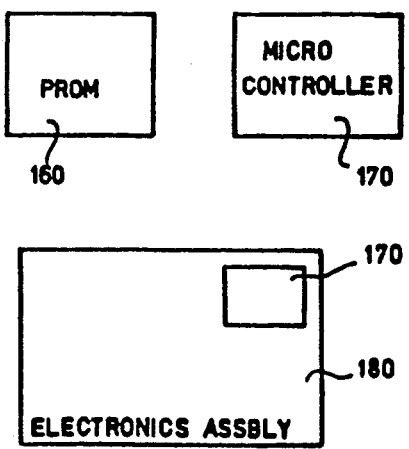
FIG. 10
FIG. 11

AUTOMATIC INTERNAL COMPRESSION-DISTRACTION-METHOD AND APPARATUS

This application is a continuation-in-part of U.S. patent application Ser. No. 07/548,814, filed Jul. 6, 1990 and is commonly assigned therewith.

FIELD OF THE INVENTION

The present invention is directed to medical equipment used in orthopaedics and traumatology to treat various congenital and acquired shortenings and other defects or skeletal segments, and, more, particularly, the invention is directed to a drive system for a compression-distraction-torsion apparatus.

BACKGROUND OF THE INVENTION

U.S. Pat. No. 4,615,338 (incorporated by reference herein) to Ilizarov discloses an orthopaedic procedure employing an external device which fixes to the bone by means of slender pins and which tensions or distracts the bone at a doctor-selected rate and rhythm of tensioning or distraction, which resulting growth of new bone, skin, muscle and nerves. The Ilizarov external fixation system uses a variety of perforated rings connected by graduated telescopic rods. Generally, the rods are distracted ¼ of a millimeter four times a day for a total distraction of 1 mm per day. When the desired length is achieved, the bone is then held in place to allow consolidation. The consolidation period is generally the same as the time needed for distraction, generally. Thus, for a distraction period of four weeks, the consolidation period would be four weeks, for a total treatment time of eight weeks. Research shows that a rate of distraction of 1/60 of a mm sixty times a day produces even better results than ¼ of a mm increments.

Generally, in the Ilizarov system, the nuts of the graduated telescopic rods interconnecting the support members are turned manually to cause distraction. U.S. Pat. No. 4,615,338 discloses an automatic drive system employing a lead screw mated with a ratchet wheel placed in a housing, and a pawl interacting with teeth of the ratchet wheel to drive the ratchet wheel to adjust the length of the telescopic rod.

SUMMARY OF THE INVENTION

It is an object of the present invention to provide an autodistractor system which employs at least one motor to adjust the length of a rod member in a Ilizarov-type system, and a programmable controller which controls the motor or motors and stores information regarding the rod length adjustment.

It is a further object of the present invention to provide a compression-distraction-torsion apparatus employing a programmable controller whereby a doctor can adapt the system to particular needs based on the number of motors, the process type (i.e., compression, distraction or torsion), the number of millimeters advancement per day, the number of times the motor or motors are to be advanced per day to achieve the desired total daily advancement, and the total movement required for the overall treatment.

The above and further objects of the present invention are achieved in a surgical, orthopaedic apparatus which comprises a plurality of support members; a plurality of rods interconnecting the support members, the rods comprising adjustment means for enabling the rod length to be adjusted; a plurality of pins attached to the support members, the pins comprising means for controlling the adjustment means of the rods to adjust the rod length of the rods to alter the relative positions of the support members. The drive means comprises at least one motor (which may be a digital motor) for incrementally adjusting the adjustment means to stepwise adjust the rod length, and a controller means for providing pulses to the motor to control the incremental adjustments of the rod length and for storing information regarding the number of stepwise adjustments of the rod length by the motor during an overall treatment procedure. The invention typically includes a plurality of motors corresponding in number to the plurality of rod members.

The invention can further include a feedback sensor means for sensing the amount of adjustment of the length of the rods and for providing data representing the sensed amount of adjustment to the controller means. The controller means can further include a comparator means for comparing the information regarding the number of stepwise adjustments with the data representing the sensed amount of adjustment.

The apparatus can further include a manual control means for controlling the adjustment means of the rods to adjust the rod length in order to alter the relative positions of the support members, and a switch means for selecting between a manual mode in which only the manual control means controls the adjustment means of the rods and an automatic mode in which only the automatic drive means controls the adjustment means.

The support members can comprise a ring having a plurality of radially extending through holes having said pins extending therethrough. The rods can comprise a graduated telescopic rod, and the adjustment means of the rods can comprise a nut. The motors can be mounted on the graduated telescopic rods.

The apparatus can include a gear mount ring mounted around the nut of the telescopic rods, with the gear mount ring comprising, on one end, a detent latching loop engaged with a projection of the nut such that the gear mount ring and the nut are rotatable in concert with one another and, on its other end, an internal gear ring. A gear box is connected to the motor and includes an output gear comprising a gear means for engagement with the internal gear ring of the gear mount ring. The apparatus can further include means for enabling the gear mount ring to disengage from the output gear while maintaining engagement between the detent latching loop and the projection of the nut. As a result, when the gear mount ring is disengaged from the output gear, a manual mode is provided in which the nut can be manually rotated, and when the gear mount ring is engaged with the output gear, an automatic mode is provided in which the nut can be rotated by the automatic drive means.

The feedback sensor means can be an infrared sensor or a magnetic reed switch.

The apparatus can further include a display means, connected to the controller means, for displaying a representation of the information regarding the number of stepwise adjustments of the rod length during the overall treatment procedure.

The apparatus can also comprise a contraction/distraction system which is placed inside a bone of a patient, such as a femur, and which includes a battery operated controller with motor drive which is connected to the internal orthopaedic apparatus by means of a flexible drive shaft. The internal orthopaedic apparatus may be constructed from a hollow telescoping rod having an internal drive screw which, when rotated by the external motor by means of the flexible shaft, provides the compression and distraction forces. The internal orthopaedic apparatus may be secured to the femur by means of interlocking screws and/or bolts placed through the femur and the internal orthopaedic apparatus.

According to the invention there is also provided a method of controlling a surgical, orthopaedic apparatus which includes a plurality of support members; a plurality of rods interconnecting the support members, the rods comprising adjustment means for enabling the rod length to be adjusted; and a plurality of pins attached to the support members, the pins comprising means for passing through bone of a patient. The method comprises controlling the adjustment means of the rods to adjust the rod length to adjust the relative positions of the support members by employing a plurality of motors corresponding to the plurality of rods to incrementally adjust the adjustment means to stepwise adjust the rod length and employing a controller means to provide pulses to the motors to control the incremental adjustments of the rods and to the store information regarding the number of stepwise adjustments of the rod length by the motors.

The method can further comprise sensing the amount of adjustment of the rod length and providing data representing the sensed amount of adjustment to the controller means based on a comparison of the information regarding the number of stepwise adjustments with the data representing the sensed amount of adjustment. The method can further comprise displaying a representation of the information regarding the number of stepwise adjustments of the rod length.

The method can further comprise providing a test pulse to each one of the motors and checking whether each of the motors responds properly to the pulse. The method can further comprise (i) storing in a counter a predetermined count representing a total number of pulses required to be sent to each motor to step the motor a required amount at each advance cycle and a total cycle count representing a number of advance cycles required for each of the motors to achieve a desired total treatment movements; (ii) providing a control pulse to a first one of the motors to advance it one increment; (iii) determining whether the first one of the motors is turned on in response to the control pulse; (iv) turning off the first one of the motors; (v) determining whether the first one of the motors is turned off; (vi) decrementing the predetermined count stored in step (i) to provide a decremented count responsive to the first one of the motors being advanced one increment; and (vii) checking whether the decremented count obtained in step (vi) is greater than zero, and if so, repeating steps (ii)-(vi) with respect to the first one of said digital motors. The method can further comprise, responsive to a determination that the decremented count obtained in step (vi) is equal to zero, storing again in the counter the predetermined count and performing steps (i)-(vii) successively with respect to all other ones of the motors to complete an advance cycle for the motors.

The method can further comprise counting a number of the advance cycles carried out with respect to the motors; comparing the number of advance cycles with the total cycle count representing the number of advance cycles required to achieved the desired total treatment movement; performing steps (i)-(vii) with respect to the motors to carry out another advance cycle after a predetermined time delay responsive to a determination that the number of advance cycles is less than the total cycle count; and terminating the treatment responsive to a determination that the number of advance cycles is equal to the total cycle count.

The above and other objects, advantages and features of the invention will be more fully understood when considered in conjunction with the following discussion and to the attached drawings.

BRIEF DESCRIPTION OF THE DRAWINGS

FIGS. 1A-1D illustrate the autodistractor/compressor motor assembly according to the invention mounted on a telescopic rod;

FIG. 2 is a top view of a gear mount ring of the FIG. 1 system;

FIG. 3 is a side view of the gear mount ring;

FIG. 4 is another side view of the gear mount ring illustrating the detent latching loop;

FIG. 5 illustrates the motor mounts;

FIG. 10 illustrates the interactive setup procedure;

FIG. 11 shows a microcontroller;

DETAILED DESCRIPTION OF THE PREFERRED EMBODIMENTS

Figure 6:
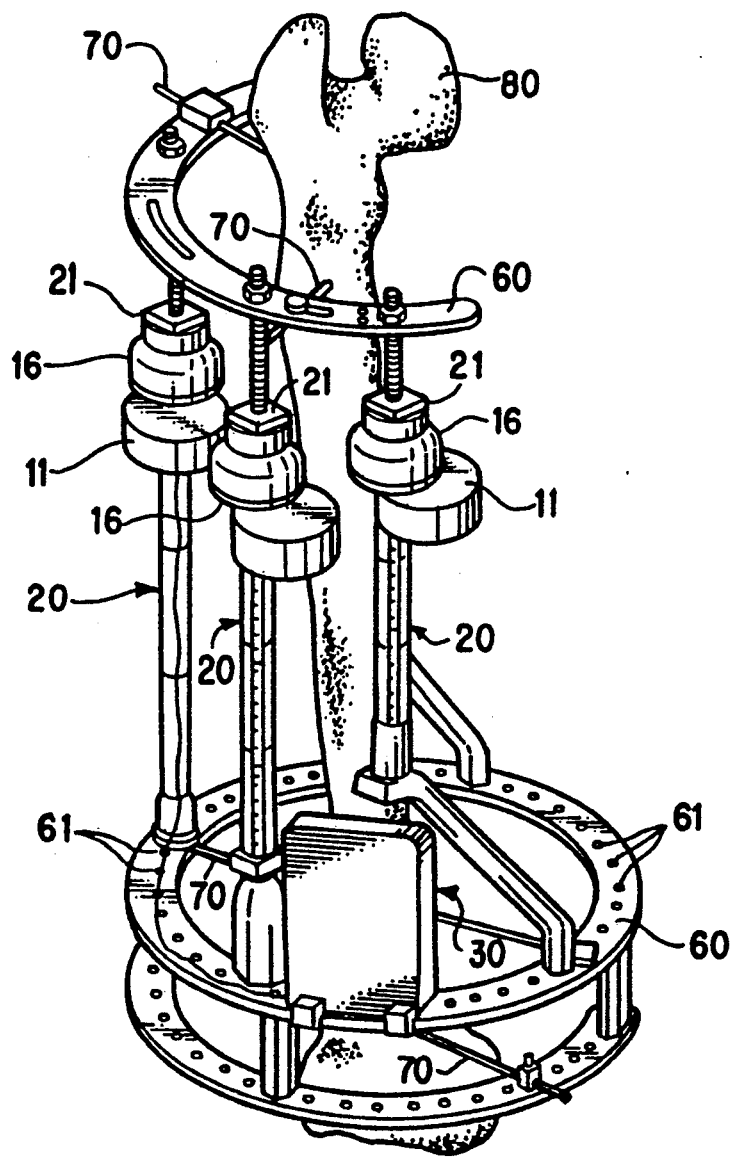
FIG. 6 illustrates the overall autodistractor/compressor/torsioner system according to the invention.

FIGS. 1A-1D show the autodistractor/compressor/torsioner motor assembly 10 according to the invention mounted on a telescopic rod 20. The assembly includes a motor 11 (which may be a digital motor) mounted via motor mount 14 onto rod 20, gear box 13 associated with motor 11, and an output gear 15 controlled by motor 11. A gear mount ring 17 is mounted on nut 21 of graduated telescopic rod 20. Gear mount ring 17 includes a detent latching loop 19 which engages with a projecting member 23 of nut 21 and an internal gear ring 16 which engages with output gear 15 of the digital motor-gear box combination. Member 23 is a spring loaded detent latch which locks at 90° rotations of nut 21. Detent latching loop 19 holds the latch open to allow rotation of nut 21 by the motor means. When gear mount ring 17 is in the manual mode, latch 23 performs normally. Set screw 18 passes through a through bore in gear mount ring 17 and abuts against nut 21. In this manner, motor 11 controls rotation of gear mount ring 17 and, in turn, nut 21. Gear mount ring 17 can be manually moved in the direction of arrow A so as to provide a switching means to select between a manual mode in which internal gear ring 16 is disengaged from output gear 15 so that nut 21 can be rotated manually and an automatic mode in which internal gear ring 17 is coupled with output gear 15 such that motor 11 is able to rotate nut 21.

A programmable controller 30 is connected to motor 11 to provide signals thereto to control the stepwise or incremental adjustments of nut 21 and, hence, of the length of rod 20. As described in detailed below, controller 30 also stores information regarding the number of stepwise adjustments of the rod length by motor 11 during the overall treatment procedure. This information is converted into a format readily comprehensible by a doctor and displayed on a display 140 (see FIG. 7) to enable determination of the progress of the overall treatment.

A feedback sensor 40 is provided to sense the actual amount of physical adjustment of the length of rod 20. Sensor 40 is preferably an infrared sensor, but may also be a magnetic reed sensor. In the magnetic sensor embodiment, a magnet is mounted on e.g., gear 15, ring 17 or nut 21; when the magnet lines up with the magnetic reed switch, a signal is sent back to controller 30. The magnetic sensor embodiment, however, is not preferred due to its sensitivity to the presence of external electromagnetic fields. In the infrared embodiment, sensor 40 receives infrared light reflected off a reflector 40A mounted, e.g., on gear mount ring 17. Reflector 40A could also be mounted, e.g., on nut 21 or gear 15. Specifically, sensor 40 enables controller 30 to count and store the number of revolutions of gear mount ring 17 and hence nut 21. Sensor 40 thus provides data to controller 30 representing the sensed amount of adjustment of the rod length. Controller 30 includes a means for comparing this sensed adjustment amount with the stored information regarding the number of stepwise adjustments of the rod length. If a non-equivalence is detected, an investigation of its cause will be carried out.

FIGS. 2-4 show details of gear mount ring 17, including an internal gear ring 16, a detent latching loop 19 and a set screw 18. FIG. 5 illustrates the particular features of motor mount 14 including a through bore 12A for receiving motor 11 and a through bore 12B by which mount 14 is a secured to rod 20. The ends of mount 14 are clamped as illustrated.

FIG. 6 illustrates the overall autodistractor/compressor/torsioner system 50 according to the invention. This system includes a plurality of support members 60, preferably in the form of perforated rings. Rings 60 include holes 61 in which a plurality of graduated telescopic rods 20 are secured in order to interconnect support rings 60. A plurality of pins 70 are attached to the support members 60 and pass through the bone 80 of a patient. FIG. 6 shows a plurality of motors 11 and gear mount rings 17 mounted on nuts 21 and rods, these elements having the same structure as that illustrated in FIG. 1. The FIG. 6 system incorporates the elements of motor assembly 10, rod 20, controller 30 and sensor 40 shown in FIGS. 1-5. Controller 30 controls each of motors 11 mounted on the plurality of rods 20 and receives feedback from sensors 40 associated with each of motors 11 as described above in connection with FIG. 1.

Figure 7:
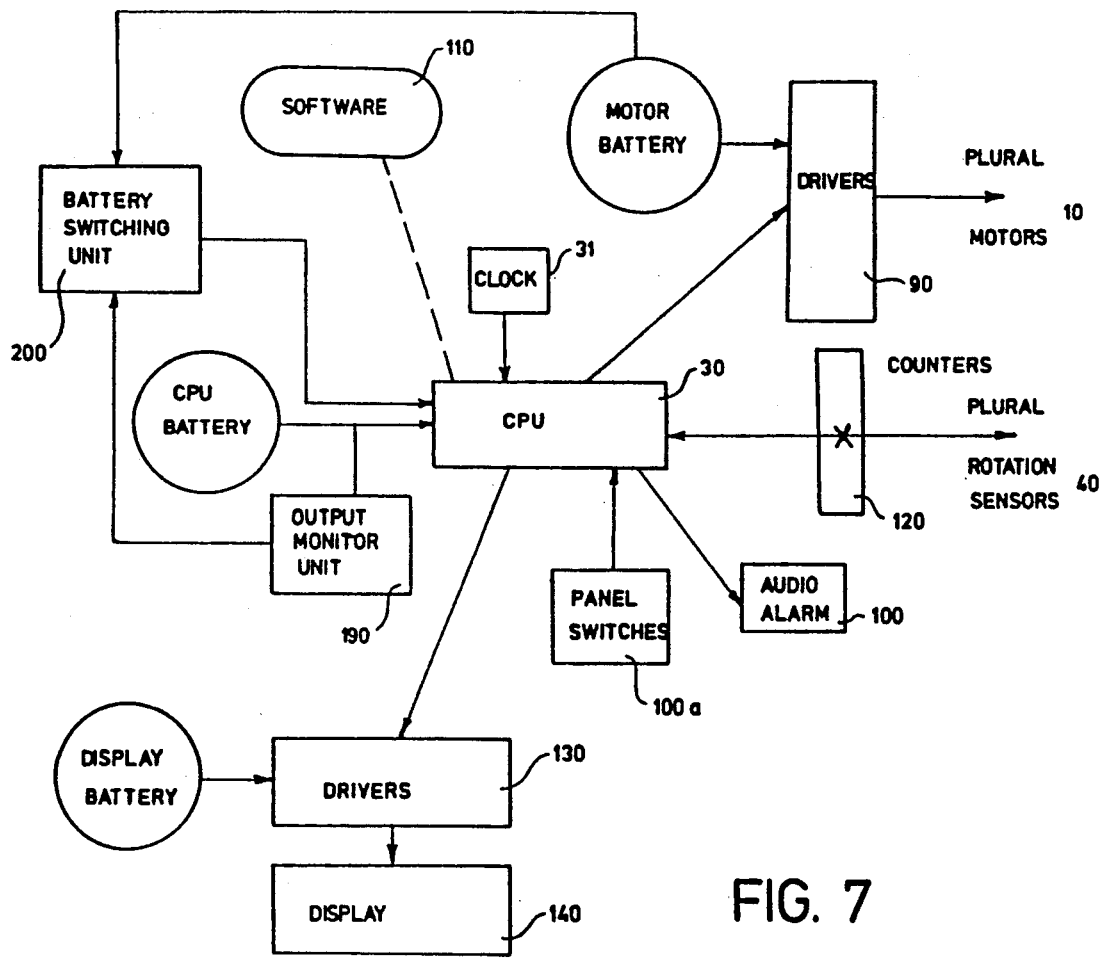
FIG. 7 illustrates the autodistractor/compressor/torsioner system in block diagram form.
Figure 8:
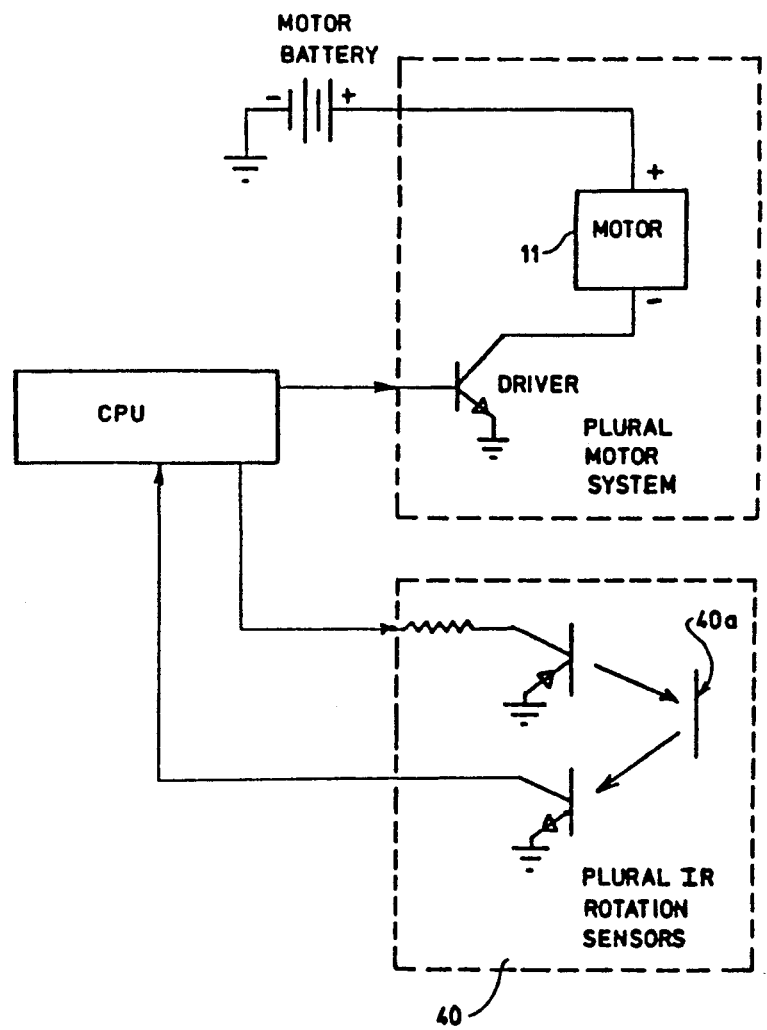
FIG. 8 illustrates further details of the system in partial block diagram format.

FIGS. 7 and 8 illustrate the autodistractor/compressor/torsioner system in block diagram form. Controller 30 is in the form a of CPU synchronized with a clock 31. Software 110 controls controller 30 as described in detail below in connection with the flow charts of FIGS. 13-19. Sensor 40 provides feedback data regarding the actual position of rods 20; this data is stored in counters 120 and fed back to CPU 30. CPU 30 also provides data to display drivers 130 which drive display 140 to display the data in a format readily comprehensive to the doctor to enable determination of the progress of the overall treatment. Panel switches 100A include a display switch to control actuation of display 140. CPU 30 also provides output signals to drivers 90 for motors 11 to control the stepwise adjustments of rods 20.

As shown in FIG. 7, an output monitor unit 190 monitors the output from the CPU battery. If this output level falls below a predetermined threshold, monitor unit 190 sends a signal to battery switching unit 200 which is connected to the motor battery. This signal provided by monitor unit 190 to switching unit 200 causes unit 200 to switch the output from the motor battery to CPU 30. This provides protection against system failure in the event of failure of the CPU battery.

Figure 30:
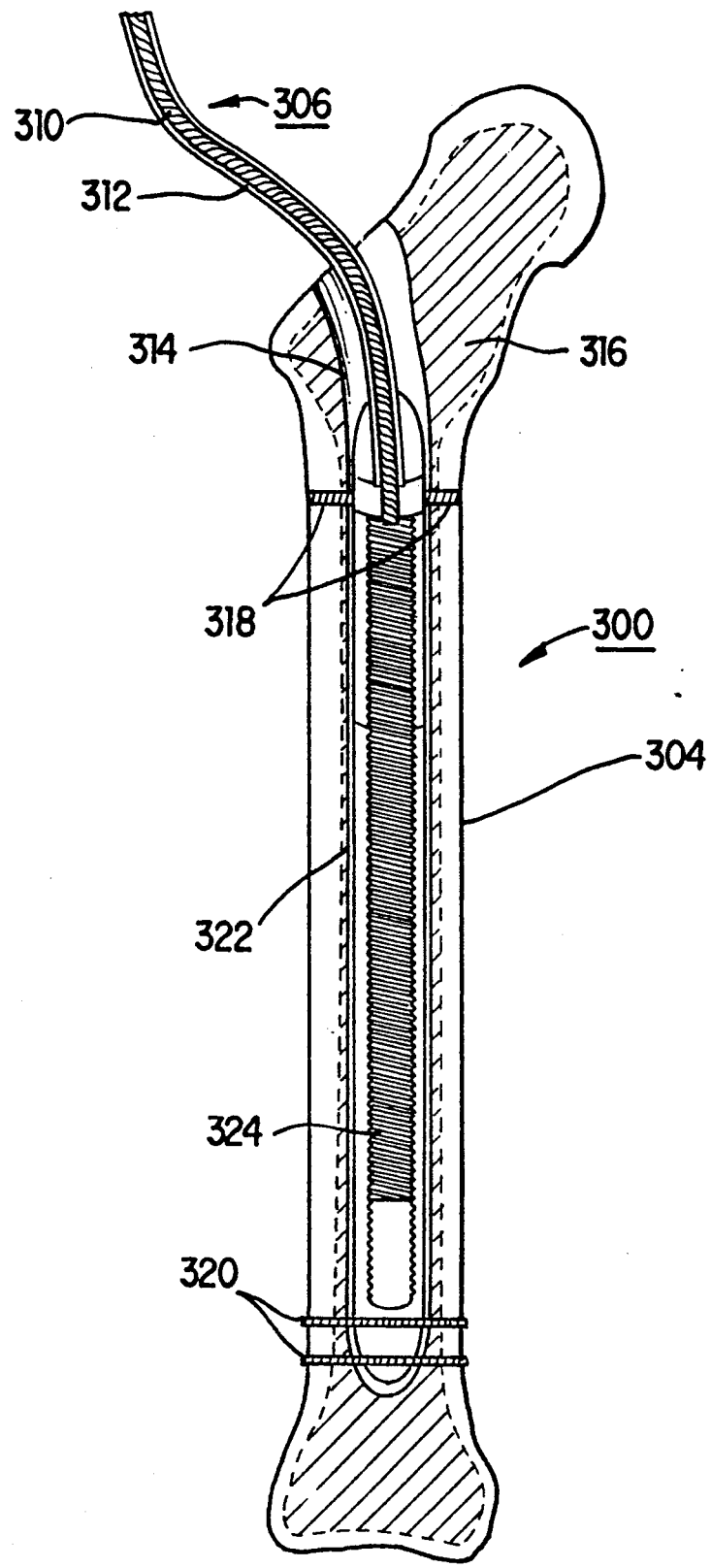
FIG. 30 illustrates an alternate autodistractor/compressor assembly secured internally in a bone of a patient.
Figure 31:
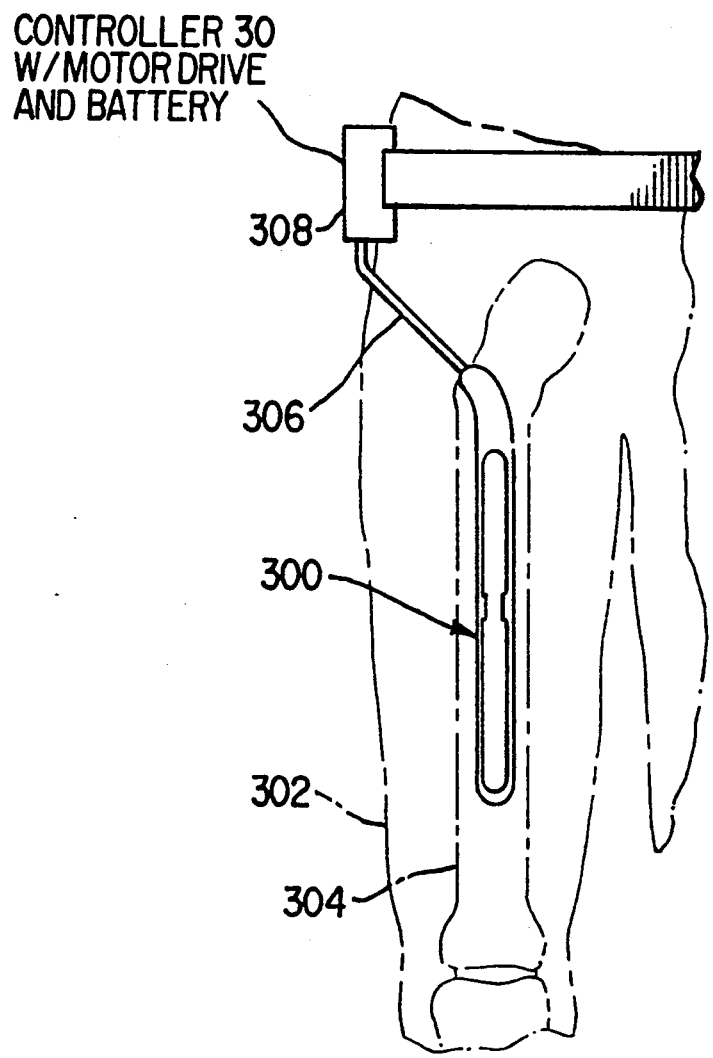
FIG. 31 illustrates the autodistractor/compressor of FIG. 30 together with the attached controller, drive motor and battery.
Figure 32:
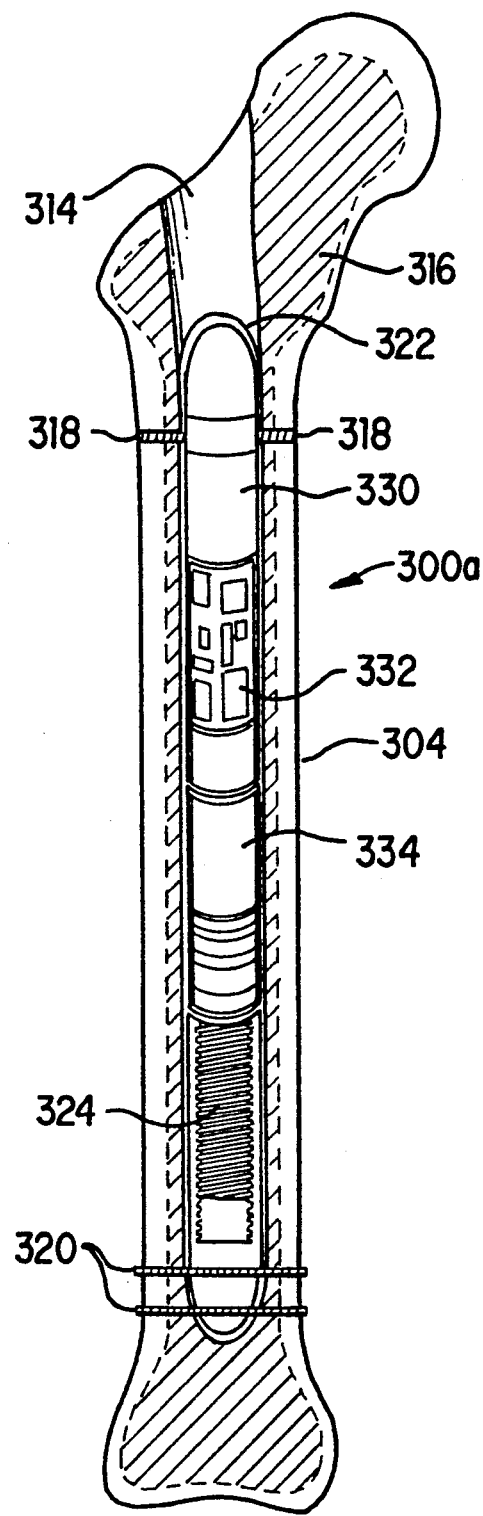
FIG. 32 illustrates an alternate embodiment of the autodistractor/compressor assembly of FIG. 30 in which the entire assembly is mounted internally in a bone of a patient.

FIGS. 30-31 and 32 illustrate two embodiments of an internal autodistractor/compressor system in diagram form. FIG. 31 shows a first embodiment of an internal autodistractor/compressor system installed in the femur 304 of the leg 302 of a patient. The internal distractor assembly 300 which is formed of two overlapping cylindrical members which form a telescoping rod, as will be described later in connection with FIG. 30, is implanted in the femur 304 by a physician. A controller 30 with drive motor and battery for operating both the controller 30 and the motor drive is affixed to the outside of a patient by means of, for example, a belt. A shielded flexible cable 306 enters the patient and is used to transmit the rotational movement of the motor drive to the internal autodistractor/compressor assembly 300.

FIG. 30 shows the internal autodistractor/compressor assembly 300 in additional detail. The internal autodistractor/compressor assembly 300, as previously described, is connected to the controller and motor drive assembly 308 shown in FIG. 1 by means of a shielded flexible cable 306. The shielded flexible cable 306 is formed from a flexible drive shaft 310 contained within sheathing 312. The sheathing 312 is used to both contain the flexible drive shaft 310 and to enable suturing around the drive shaft 310 to close the incision formed during implantation of the internal autodistractor/compressor assembly 300.

The internal autodistractor/compressor assembly 300 is placed into the bone of a patient, for example, the femur 304 as illustrated, by, for example, an orthopaedic surgeon. A cavity 314 is opened by a physician in the medullary canal 316 in order to insert the internal autodistractor/compressor assembly 300 into the femur.

The internal autodistractor/compressor assembly 300 is secured within the femur by a pair of interlocking screws 318 at the top of the assembly 300 and by a pair of interlocking bolts 320 which pass through the bottom of the assembly 300 and secure it to the femur 304.

As previously described, the internal autodistractor/compressor assembly 300 is formed from a telescoping internally threaded rod 322 formed in two sections, one slightly overlapping the other such that, when driven by the motor drive unit, the two sections of the telescoping rod 322 will move over each other. The flexible drive shaft 310 is connected to drive a drive screw 324 which mates with the internal threads of the telescoping rod 322. Preferably, the drive screw 324 utilizes an "acme" thread type. The "acme" thread type is utilized in order to maximize energy transfer and minimize friction within the mechanical components of the internal autodistractor/compressor assembly 300. Alternatively, the drive screw 324 may utilize a "V" or other thread type.

FIG. 32 shows an alternate internal autodistractor/compressor 300a to that shown in FIGS. 30 and 31. Where applicable, like elements have been labelled by like reference numbers. The autodistractor/compressor assembly 300a shown in FIG. 32 is fully implantable in the patient's bone. The internal autodistractor/compressor assembly 300a includes an internally mounted power supply 330, an internally mounted electronic control/communication assembly 332 and an internally mounted motor/gear train 334. The autodistractor/compressor assembly 300a therefore includes all of the motor drive, controller and battery functions of the autodistractor/compressor assembly 300 of FIGS. 30 and 31 in a surgically fully implantable unit. The unit may be surgically implanted within the body during the distraction portion of treatment. The use of a fully implantable autodistractor/compressor assembly 300a may be preferable to the hybrid system shown in FIGS. 30 and 31 because it eliminates the infection potential present at the entry point of the flexible cable 312 into the body.

The electronic control/communication assembly 332 includes a communications link which utilizes either radio frequency or electromagnetic field signals to allow a physician to adjust the rate and rhythm of distraction from outside of the body. The fully implantable internal autodistractor/compressor assembly 300a may be encased in ULTEM plastic, which is an accepted plastic used for medical implants, and is waterproof as well as inert to the body's systems.

Although the use of the internal autodistractor/compressor system is described in connection with its use in a human patient, it also can be utilized in connection with non-human patients, such as animals. Likewise, the autodistractor/compressor/torsioner system described herein can be utilized other than human patients.

With reference to FIGS. 13-29, the operation of the automatic distractor/compression/torsion system according to the invention, is as follows.

OVERVIEW

The setup program is designed to operate on a personal computer (PC). This allows the doctor to customize the software on the microcontroller for each particular distraction/compression/torsion case. The setup program will ask for and accept input on the number of motors, the process, i.e., compression, distraction or torsion, the number of millimeters movement per day, the number of times the motor will advance per day to achieve the required movement per day and the total movement required for the overall treatment. The setup program also collects information on the patient's name, doctor's name, chip number, date and other relevant information. Hard copies are generated of all inputted information to allow the doctor to verify the input, identify the microprocessor, record the settings for patient records, and keep other necessary records.

After the microcontroller software has been downloaded and verified and the microcontroller has been inserted into the electronics assembly, the software performs an initial check to be certain the electronics system is connected appropriately and the right chip has been inserted. If not, the software will trigger an alarm and an error code will be displayed.

If no error exists, the doctor can then actuate the start switch. The system will advance the motors and check to be certain all the motors are functioning properly. If not, the software will shut down the motors, display an error code and trigger the alarm.

Thereafter, the software controls the movement of each motor and tests to be certain that the motor is advancing the gear the amount established in the setup program via a feedback system. The advancement tests are run on a continuing basis to prevent a "runaway" or stalled motor condition. The system will shut down the motors, display an error code, and trigger the alarm if an advancement error is detected.

The software also monitors the current supply from the batteries to the central processing unit (CPU-microcontroller), display and motors. If the current to the central processing unit is low, the software will also shift the central processing battery supply to the motor power supply.

The software allows an operator to request a display at any time. The display will cycle through the position of each motor for each display request.

The software also allows transient electromagnetic fields to create a temporary current in the motor leads without shutting the motors down or triggering the alarm. The software further allows the doctor to manually put the system on standby for adjustments or other necessary interruptions.

The software shuts the motors down, displays the completion code, and triggers the alarm when the system has achieved the total required movement for the overall treatment procedure.

DETAILED DISCUSSION

The ROMSET routine is run on the PC by the doctor and sets up EPROM microprocessor microcontroller 170 of the CPU 30. The doctor enters data in response to the queries regarding the number of motors, the direction (compression, distraction or torsion), rate (mm/day), rhythm (times/day), total movement required for the overall treatment and CPU serial number. The program then does a table computation to generate a table of values to be called in software subsequently. This is done by converting the rate, rhythm and total treatment movement input by the doctor to data which the motors can employ—i.e., how many pulses are required to advance the motor through one advance cycle and the long term time delay imposed on the motors between advance cycles in order to achieve the movement equal to the required mm's/day at the given rhythm. This table is then merged with the source code, and further processing is done as indicated in the ROMSET routine. FIGS. 10 and 11 illustrate a procedure for setting up the EPROM microprocessor via a PC 150, a PROM 160 and a microcontroller 170 which ultimately is inserted into an electronics board or assembly 180. After this loading procedure, microcontroller 170 is inserted into board 180 which in turn is installed in CPU 30. By reprogramming microcontroller 170, in the manner discussed above, the doctor is able to design a new treatment procedure as desired.

After the EPROM is programmed and installed on board 180, operation may begin. In the EPROM routine (FIG. 13) initially, at step 25, a check is done to determine whether the system is operating properly and whether the correct chip (i.e. board 180 containing microcontroller 170) has been loaded into CPU 30. If no, an error code is set and a termination routine TRMNAT (to be described in detail below) is called. If yes, at 28 a successful power-up is acknowledged via an acoustic signal and a visual display. At 29, the system waits for the doctor to flip a start switch and, thereafter, at 30, the CPU clock is synchronized with the clock in the electronics assembly 180. At 31, a single pulse is sent to each of the motors and a check is done to be certain all motors are properly connected. At 32, if the system is not indicating proper functioning, an error code is set, and the terminating routine TRMNAT is called. If the system is indicating proper functioning, this is acknowledged at 36, with an acoustic alarm and a visual display occurring. At 37, a first run flag is burned by burning a fuse in the electronics assembly.

At 13a, the total cycle count (i.e., the number of advance cycles to achieve the total treatment movement) is loaded, and at 13, the motor count (number of motors, e.g., 4) is loaded. At 14, the Mx pulse count (i.e., the number of pulses required to cause the particular motor to step the required amount at each particular advance cycle throughout the treatment) is loaded.

At 15, a given motor is turned on by sending one pulse to advance the Mx motor one increment, and at 16 a routine ONPLSTST is called to certify that the motor is on. At 17, the motor is turned off, and at 18 a routine OFFPLSTST is called to certify that the motor is off.

At 19, the counter is decremented. If the count has not reached zero, steps 14–18 are repeated. This is repeated until the count equals zero.

Thereafter, at 20 the system moves to the next motor and repeats steps 14–19 until the count for this motor reaches zero. Step 20 ends when each of the motors have been put through steps 14–19.

At 21, the CPU memory is updated with data indicating that steps 14–20 have been completed for each of the motors.

At 22, routine LTMDLY is called. This is a long-term delay routine which imposes a delay on the motors between advance cycles carried out by steps 14–20. This means all of the motors are stepped through one advance cycle, and then the long-term delay occurs. Then, each motor is again stepped through one advance cycle. The process is repeated until step 21 indicates the overall distraction, compression or torsion treatment is completed. At 23, an acknowledgment that the procedure is completed is displayed, and at 24 the termination routine TRMNAT ends the procedure.

Figure 9:
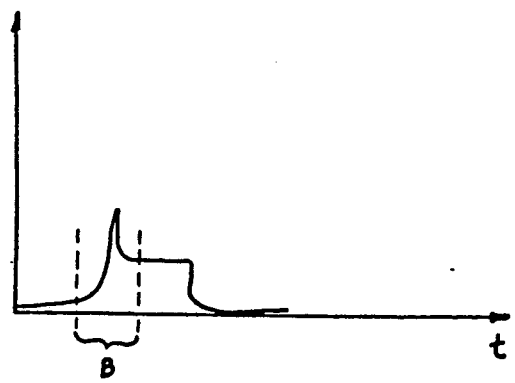
FIG. 9 illustrates a typical pulse supplied to a digital motor.

The subroutine ONPLSTST (on pulse test) is as follows. At 38, the time the motor is to be on is loaded, as obtained from the table generated during the ROMSET program. At 39, a delay is imposed to avoid checking the current pulse at the beginning of the pulse to avoid problems because of initial abnormalities. FIG. 9 shows a typical pulse, with readings from region B being avoided. The exact delay is set depending upon the type of digital motor employed.

At 40, the current flowing to the motor is checked. At 41, it is determined whether the current flow meets an acceptable limit. At 46, if the current flow is not acceptable, the "no current" error count is located. At 47, the error count is advanced by 1 to account for new "no current" error. At 48, the new "no current" error count is loaded in the memory. At 49, the acceptable error established in the ROMSET program (i.e., how many transient errors will be allowed before the movement of the system is terminated, such as 50 or 100; this allows flexibility so the doctor can make a determination depending on the environment of the patient). At 50, the new "no current" error count is checked, and a determination is made regarding whether it is below the maximum established as too many errors. At 52, if the error count is above the maximum number of allowable "no current" errors, the system physically burns a fuse designated the "open" indicator to show that, for some reason, there has been "no current" to the motor when there should have been current more than a maximum number of established times. Possible causes of the "no current" condition could be an open circuit or extensive interference from an external electrical field. At 50b, if the error count is below the maximum number of allowable "no current" errors, the system loops back prior to DECREMENT ON-TIME COUNT and the process is continued.

At 42, if the current flow is acceptable, a delay is imposed to match the time use for a "no current" decision.

At 43, the on-time count is decremented. For example, if the Mx on-time was 3 cycles through this loop, then, after the first time through this routine, the on-time count is changed to two. At 44, a check is made to determine if it is the end of the count loaded INLOAD Mx ON-TIME. At 45, at the end of the count SEDINLOAD Mx ON-TIME, a return is made to the EPROM program at step 17. At 44b, if the system is not at the end of the count SEDINLOAD Mx ON-TIME, the system loops back through the routine as shown. At 51, the "no current" error code is set into the error code memory.

The subroutine LTMDLY (long-term delay) at 99 loads the total count for the pause (e.g., 2,000) between motor movement cycles set in the ROMSET program. This will be dependent upon how many times/day the doctor desires the system to advance. At 104, the display request memory bit is loaded. At 105, it is determined whether a display request flag is in the display request bit, and, if so, at 106, the DISPLAY subroutine is called. If there is no flag, at 107, the delay count is loaded. This delay count is set in the ROMSET program to match the time required for the display subroutine.

At 108, an I/O check is made for a display request. At 109, a check is made whether the display button has been pushed and the associated electronics hardware activated. If a display request exists, at 111, the display flag is set. If no display request has been made, at 110, a delay is imposed to match the time required to set the flag.

Figure 12:
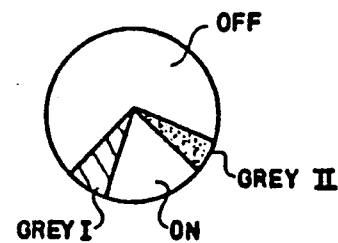
FIG. 12 illustrates grey and white parameters used in the long-term delay subroutine.
Figure 13:
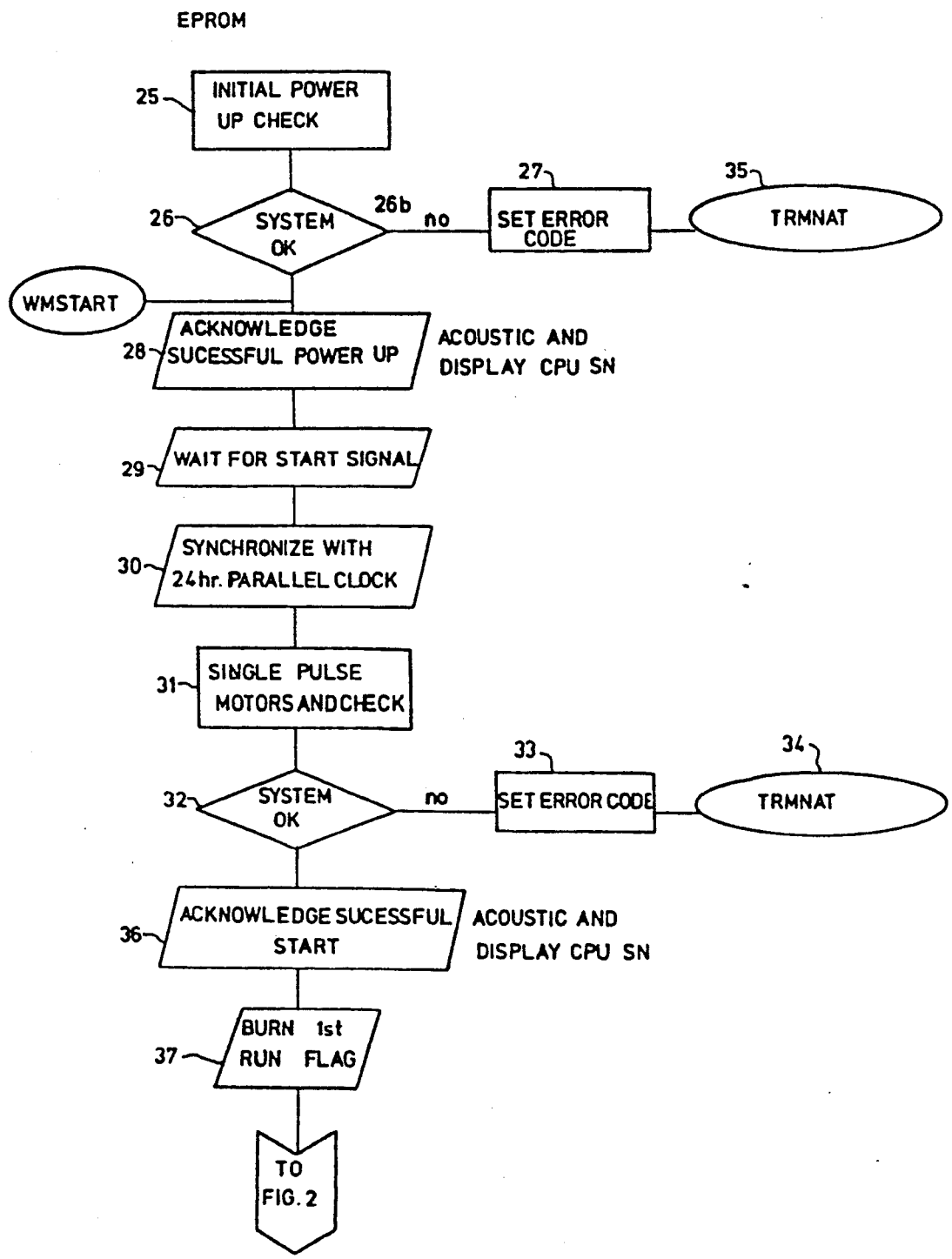
FIGS. 13-29 illustrate the operation of the automatic distraction/compression/torsion system according to the invention.
Figure 13A:
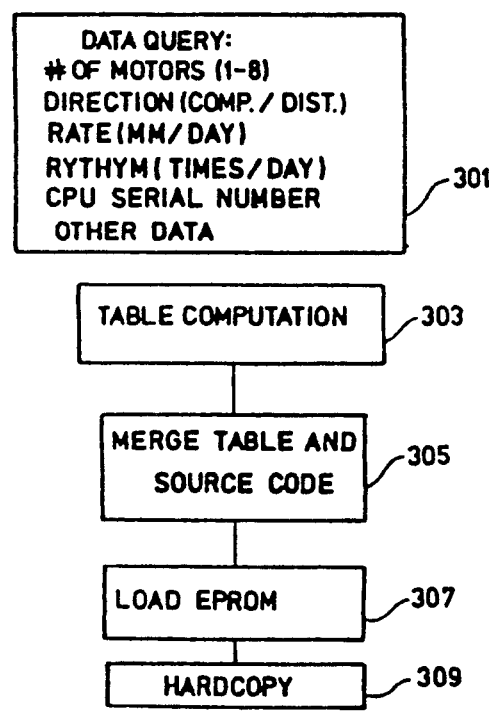
Figure 14:
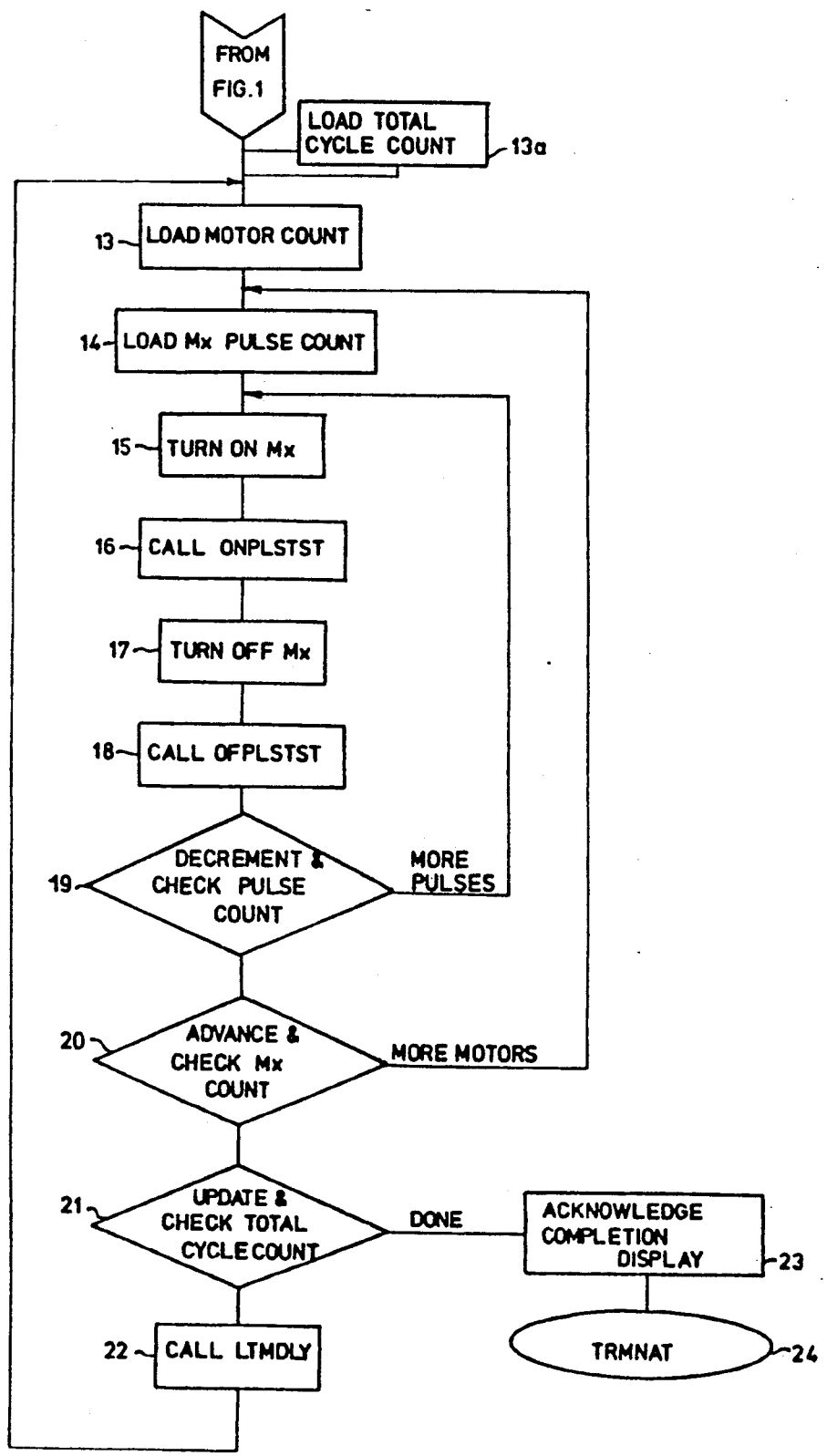
Figure 15:
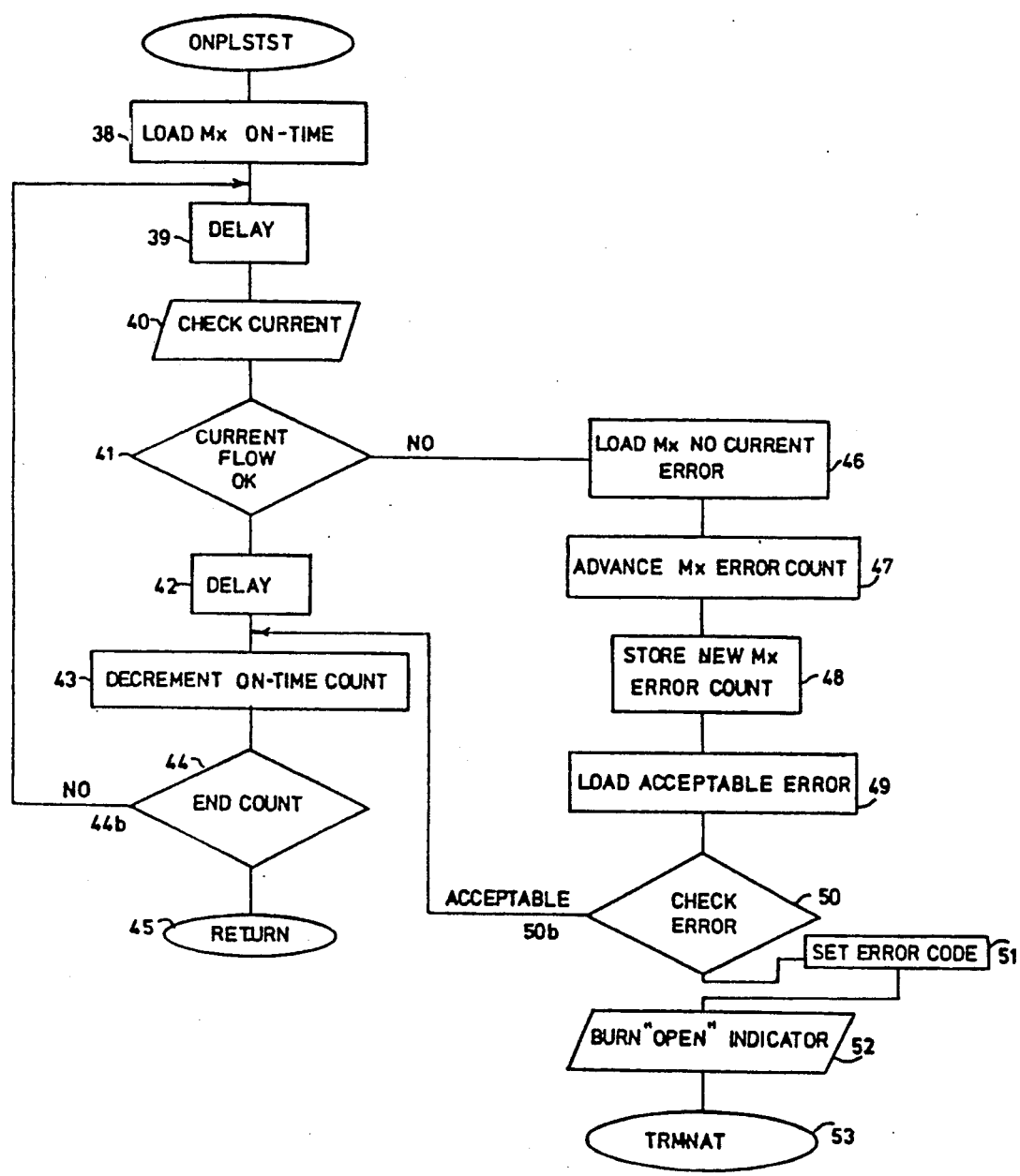
Figure 16:
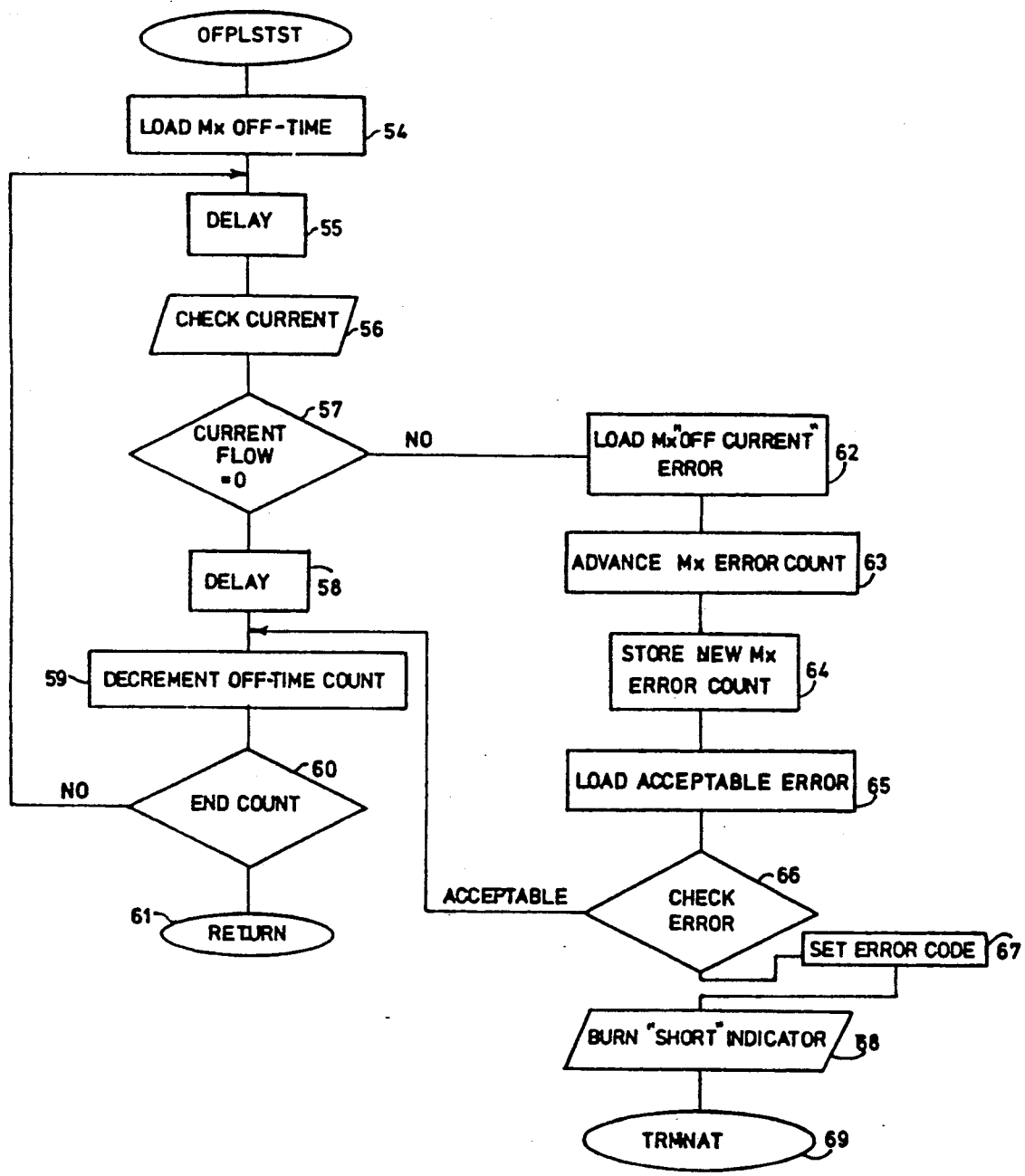
Figure 17:
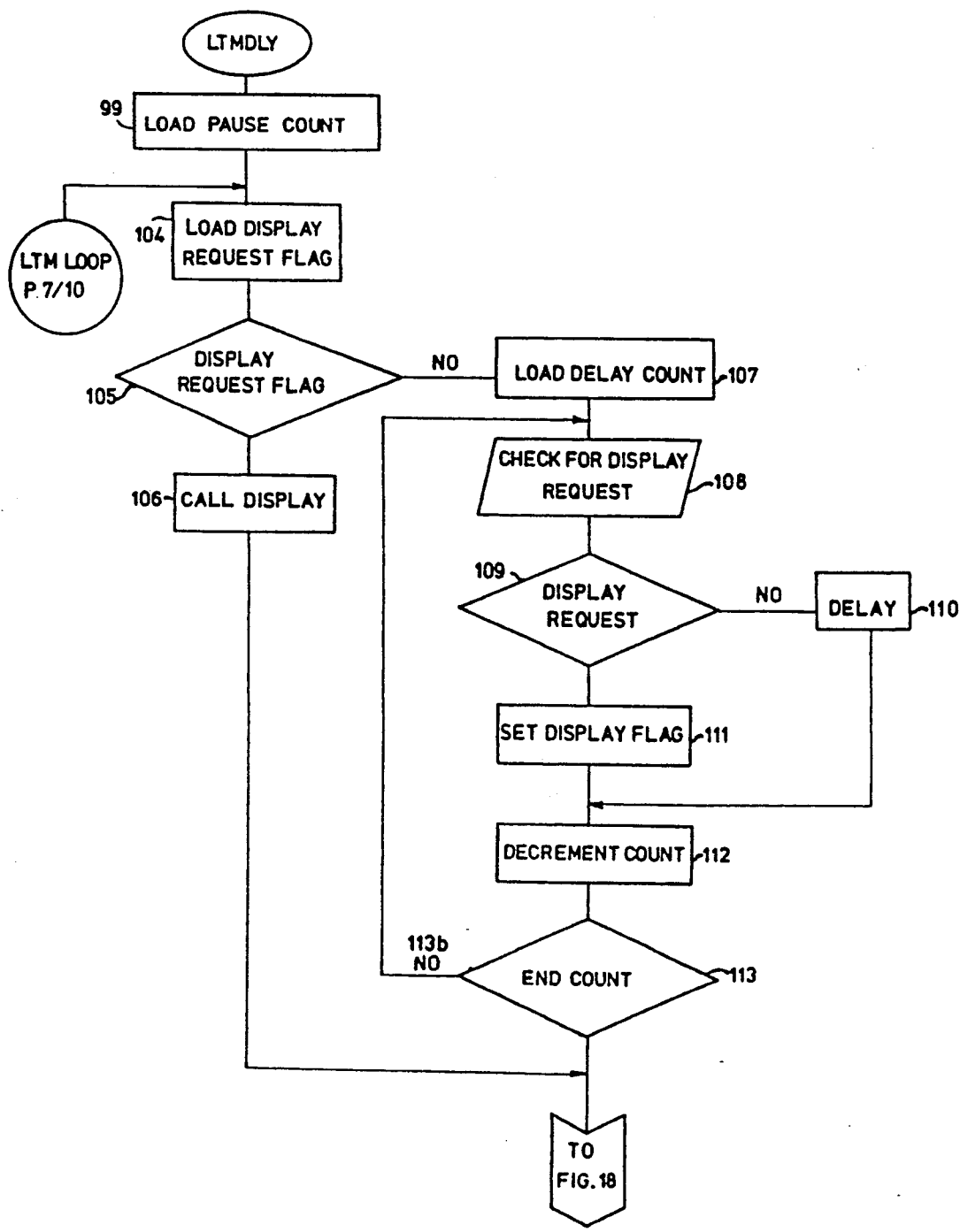
Figure 18:
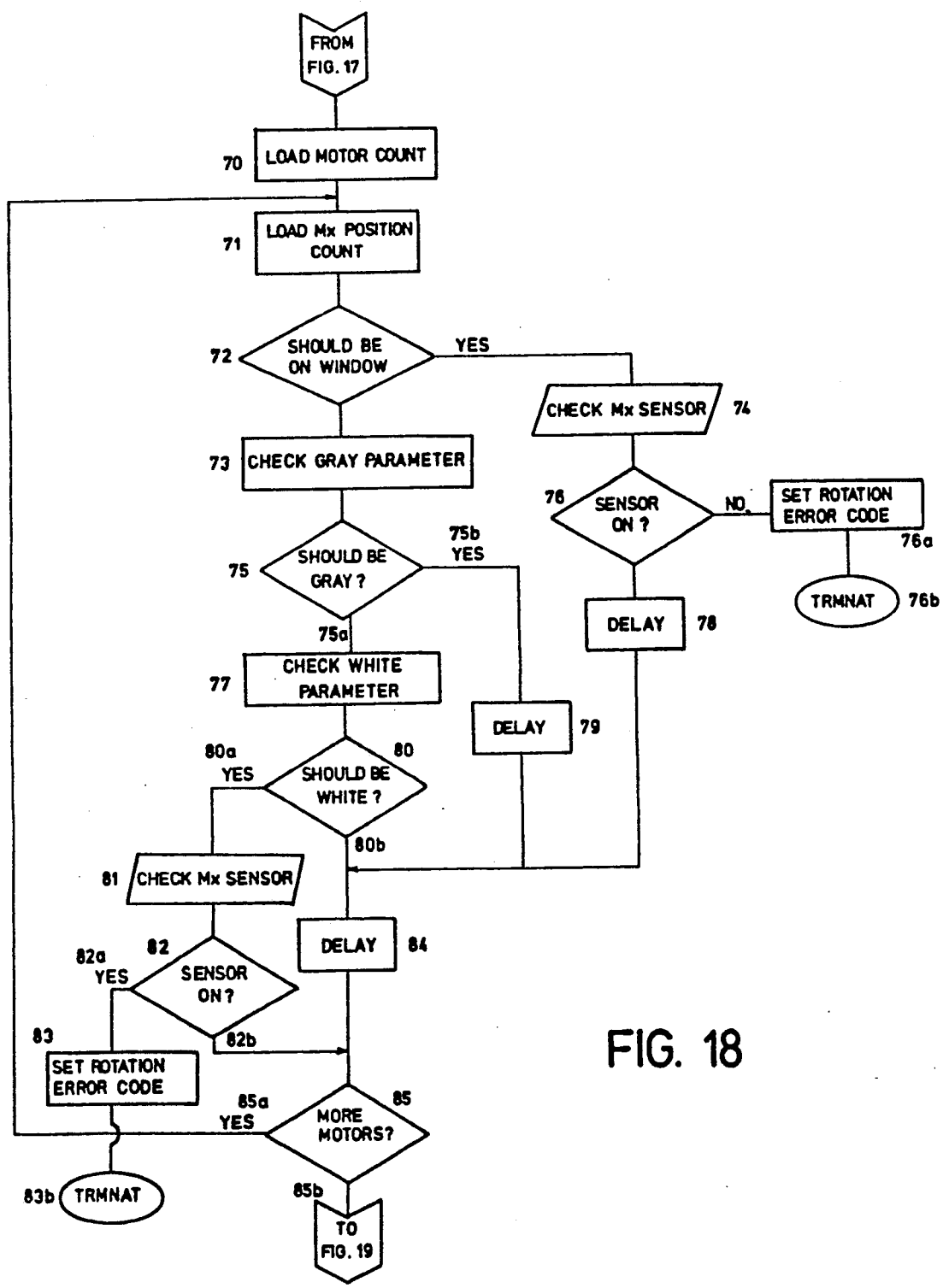
Figure 19:
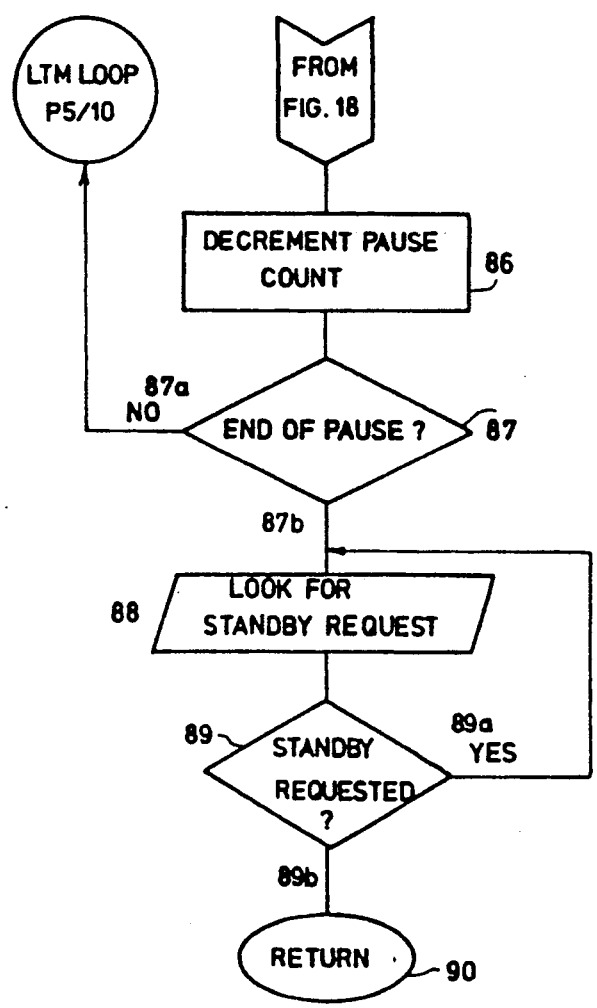
Figure 20:
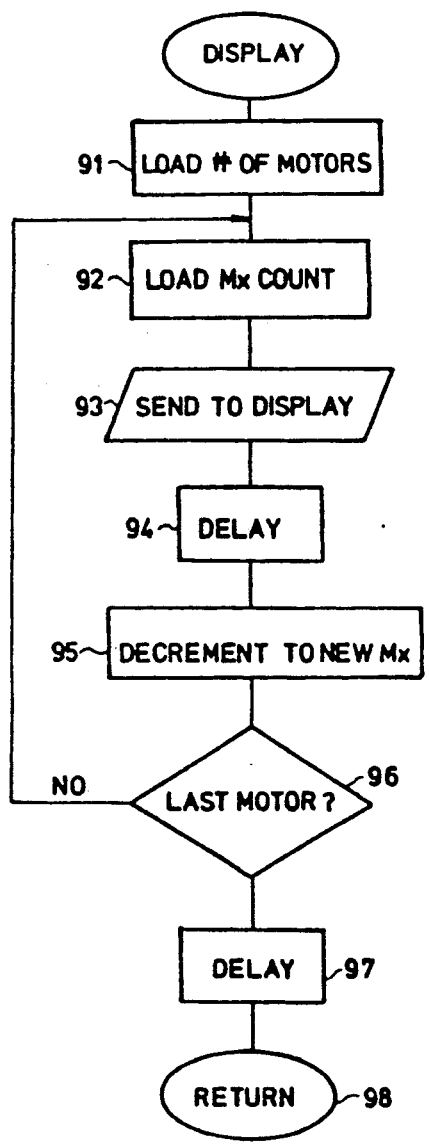
Figure 21:
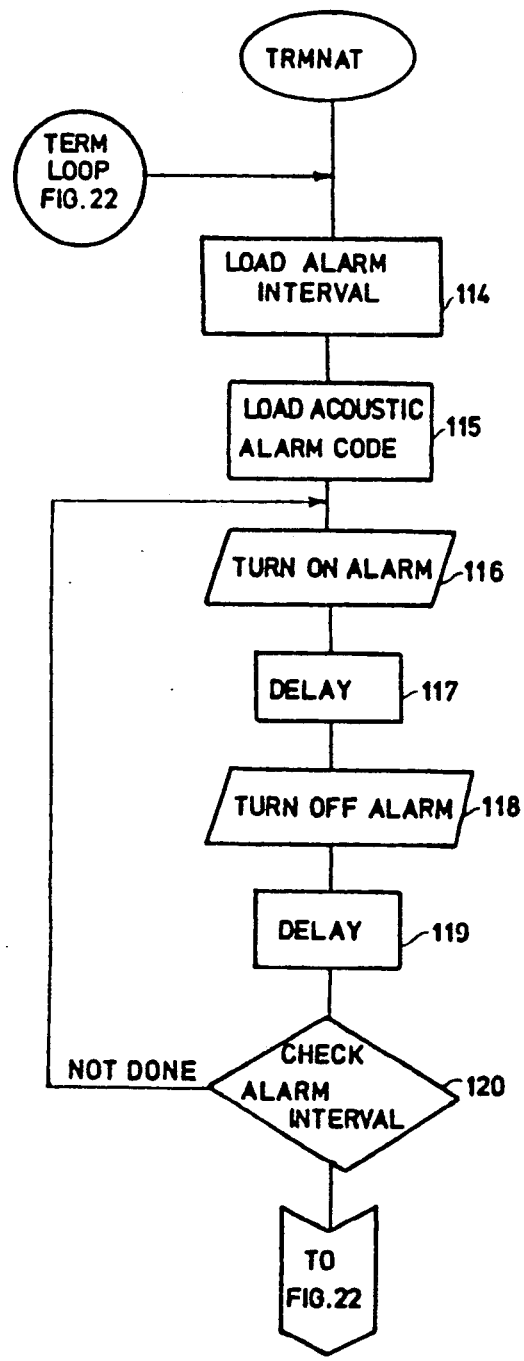
Figure 22:
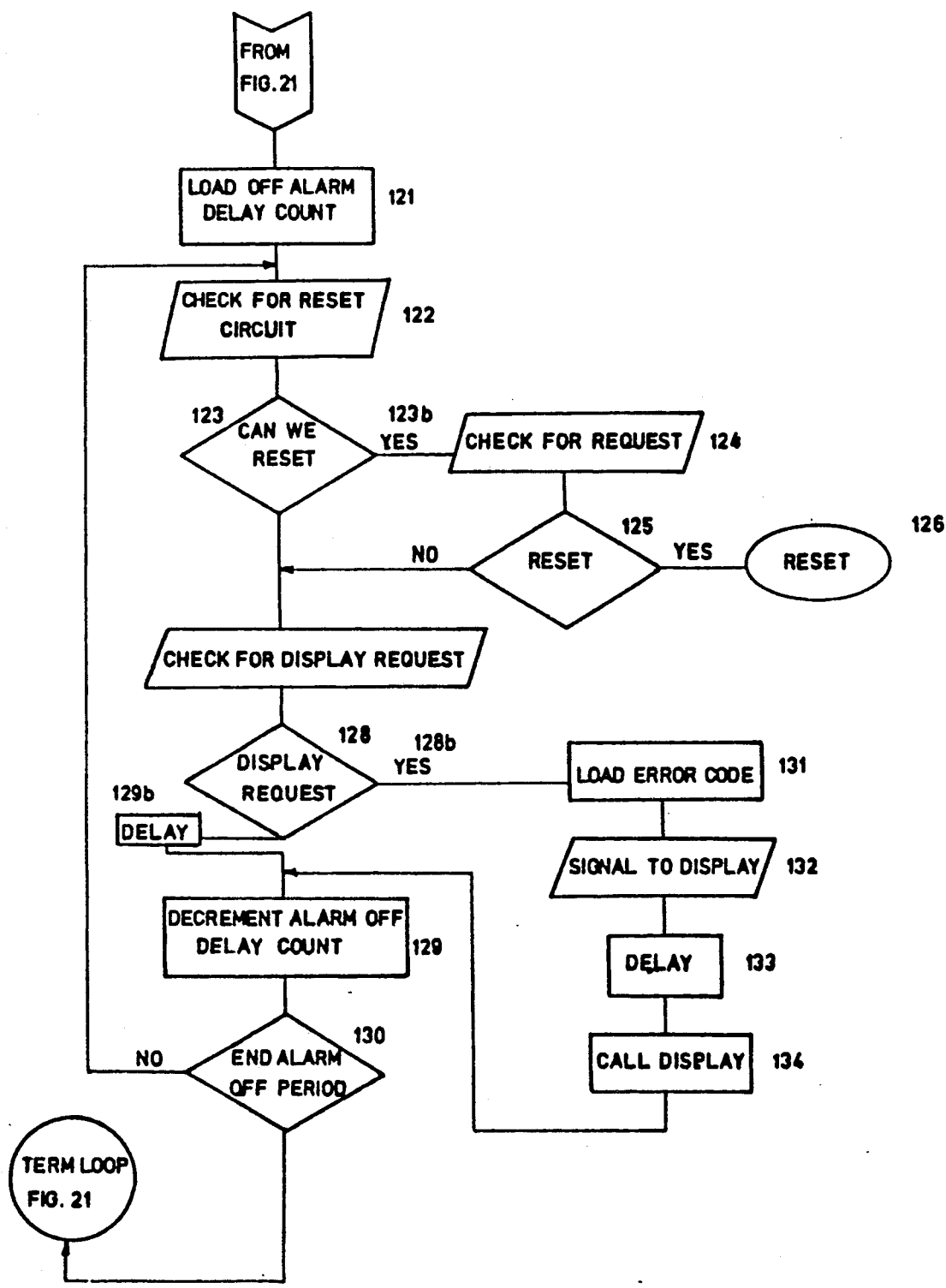
Figure 23:
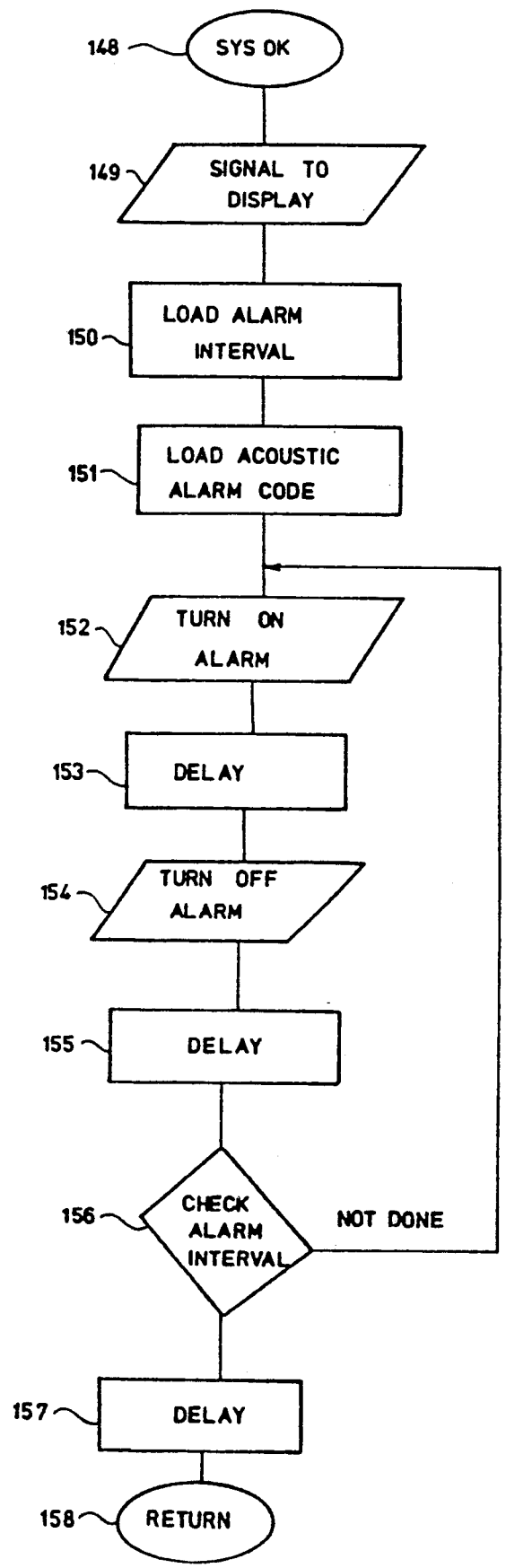
Figure 24:
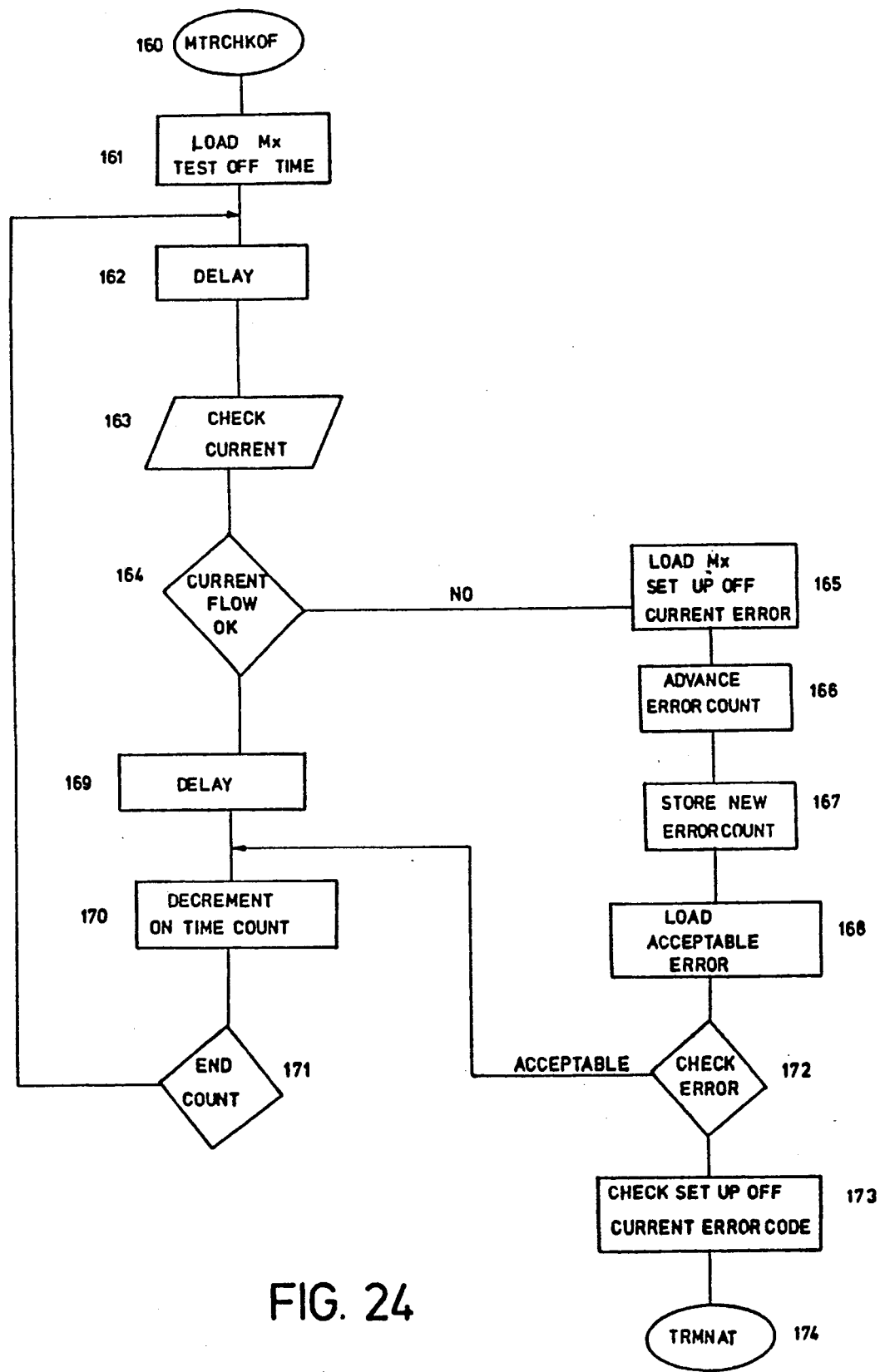
Figure 25:
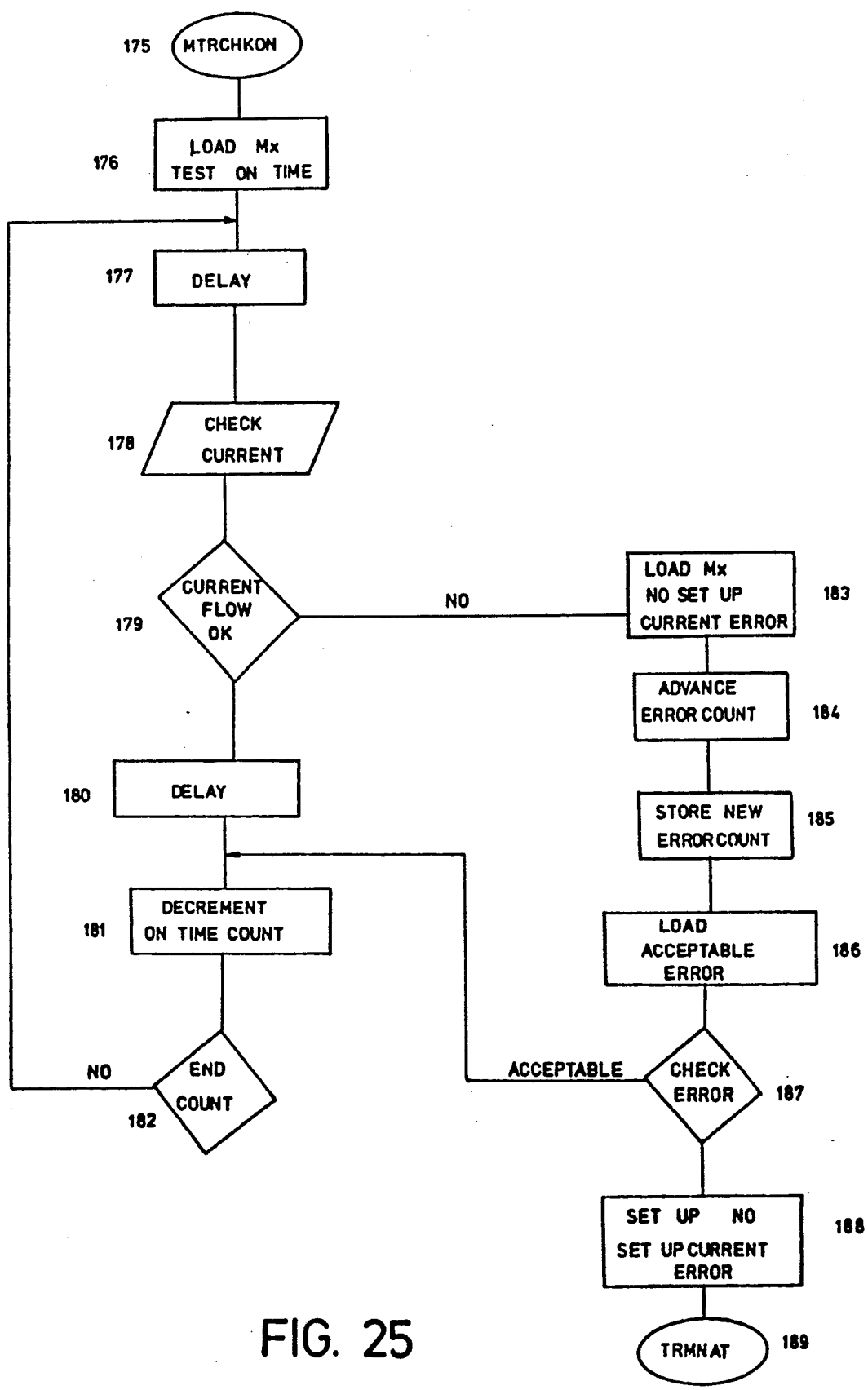
Figure 26:
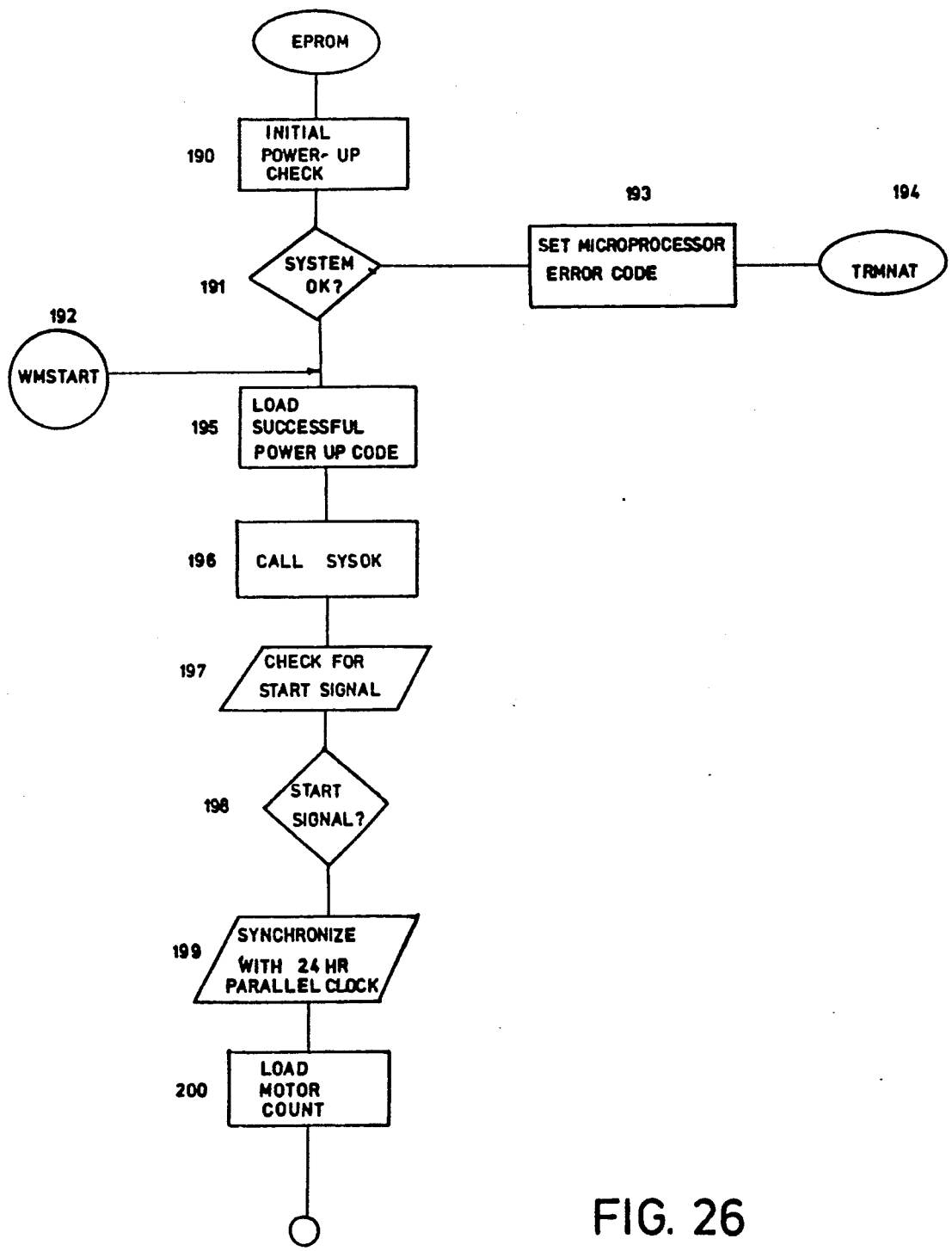
Figure 27:
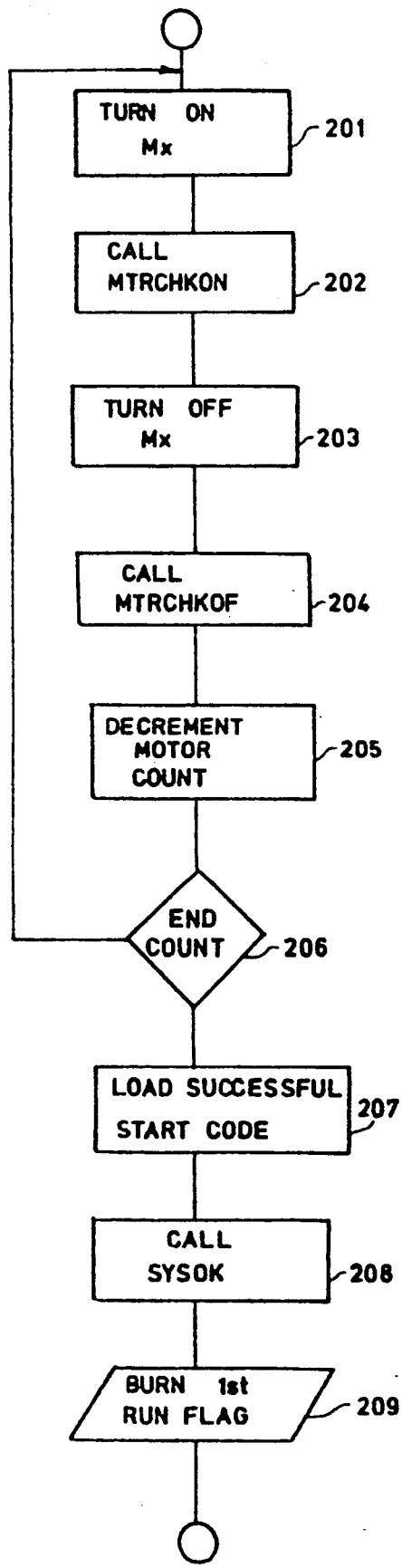
Figure 28:
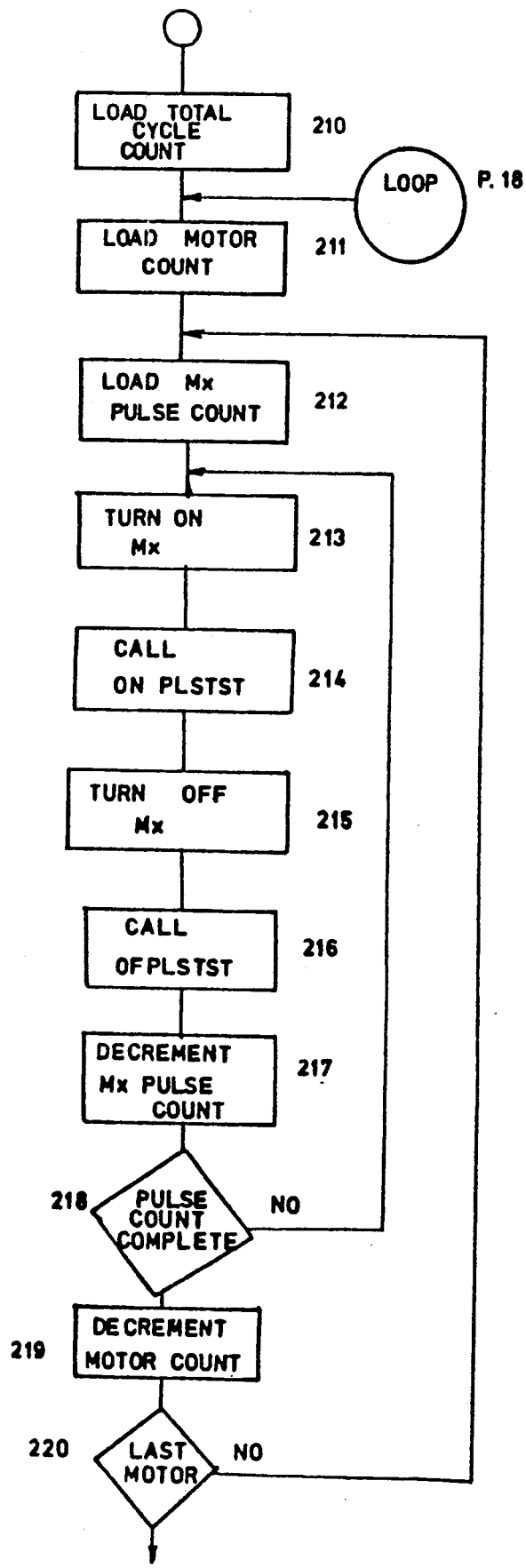
Figure 29:
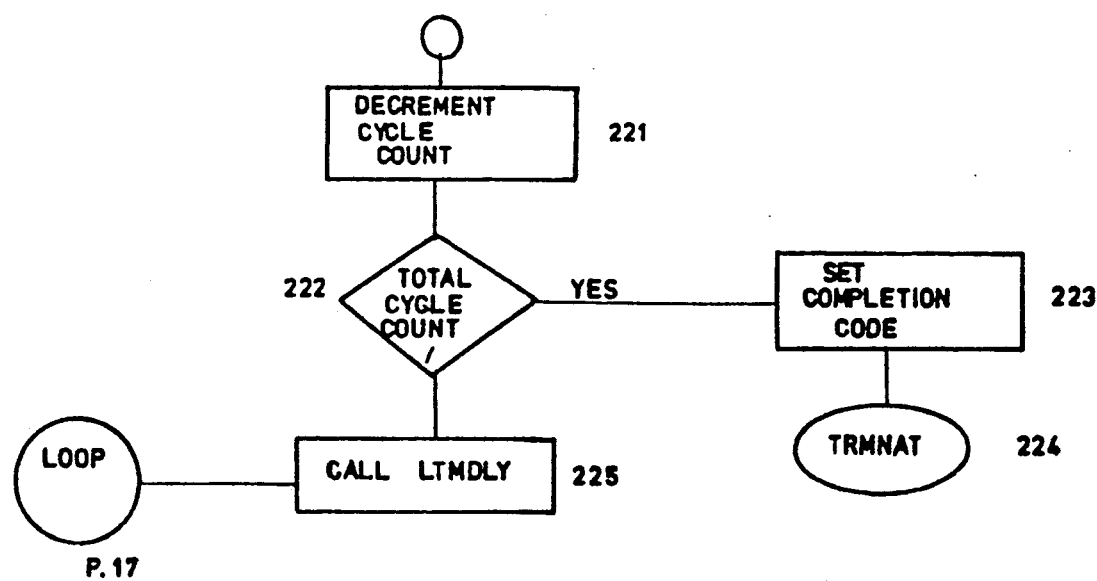

At 112, the count is decremented to account for advancement of one cycle. At 113, a check is made as to whether the value now stored in the delay indicates the end of the count. If not, at 113b, the system cycles back through the loop. If it is the end of the count, at 70, the number of motors is loaded. This is determined from the table established in the ROMSET program. At 71, the motor position count (for example, motor 1) is loaded from the table established in the ROMSET program. At 72, it is determined whether this count indicates the sensor should be ON. If the sensor is ON, the sensor is then checked at 76. If yes, at 78, a delay is imposed to match the time it takes to check other alternatives. If the sensor is OFF, at 76a, the rotation error code is set. If the sensor should not be ON based on the position count of the motor, at 73, the position parameters are loaded for the grey 1 area, i.e., between 5 and 10 is grey 1. This is illustrated in FIG. 12. At 75, a determination is made as to whether the position count corresponds to a grey 1 area. This is done by comparing the actual position count to the range for grey 1, e.g., 5–10. Thus, if the actual position count is 6, this corresponds to a grey 1 area, whereas a count of 2 would not. At 75a, it is determined that the system should be in the grey 1 area, and at 75b, it is determined that the system is not in the grey 1 area. At 79, a delay is imposed to match the time required for other checks.

At 77, the position parameters are loaded for the white area (see FIG. 12). At 80, a determination is made as to whether the system should be in the white area according to the position count. Step 80a corresponds to a count indicating a white area, and 80b indicates a count not quite corresponding to the white area. At 81-82b, a check is made as to whether the motor sensor is ON. At 83, if the sensor is not ON, the rotation error code is set. At 84, a delay count is imposed to match the time required for the computer to do other checks. At 85-85b, a determination is made as to whether all of the motors have been checked. At 86, the pause count is decremented to account for advancement of one cycle. At 87-87b, a determination is made as to whether the system is at the end of the total established pause count. At 88, the system looks for a standby request which is a jumper connected by the doctor. At 89-89b, a determination is made as to whether the standby jumper has been connected. At 90, the system is returned to load motor count (step 13).

Turning now to the subroutine DISPLAY, if the system is at the end of the count, at 91, the number of motors is loaded based on the table established by the ROMSET program. At 92, the Mx distraction count is loaded. In other words, this count indicates how far the motor has distracted the telescopic rod. At 93, an indication of the amount of the distraction is sent to the display. At 94, a delay is imposed to allow the doctor to view the distraction distance. At 95, the system decrements to the next motor sequentially, i.e., the system moves from Mx=M2 to Mx=M1. At 96, a determination is made as to whether this is the last motor, and at 97, a delay is imposed. At 98, a return is made to step 70 to load the number of motors.

With respect to the subroutine RESET, at 141, the software error flags set earlier which caused the system to call the TRMNAT subroutine are cleared. At 142, the system checks for hardware error flags. All blown fuses must be replaced before resetting the system. Blown fuses show a hardware error flag. At 143-143b, a check is made as to whether the hardware flags are OK. At 144, the "not ready" code is set for the display. At 145, the alarm interval in the TRMNAT subroutine is changed. At 146, the system goes to the TRMNAT subroutine. At 147, the system goes back to just prior to step 28, which is the acknowledged successful power-up step in the EPROM routine.

Regarding the TRMNAT subroutine, at 114, the alarm interval set in the ROMSET program is loaded and at 115, the acoustic alarm code (alarm sound) is loaded. At 116, the alarm is turned on by sending current to the alarm. Step 117 imposes a delay to allow the desired length of sound. Step 118 turns the alarm off. At 119, a delay is imposed to allow the desired length of time between alarm sounds. At 120, a determination is made as to whether the alarm has been activated enough times to meet the alarm interval from step 114. At 121, an "off alarm" delay is imposed. This is set in the ROMSET program and represents a period of time between alarms. At 122, the system checks to determine whether the setup has a reset capability from the ROMSET program. At 123, the system determines whether a reset is acceptable. AT 124, the system checks for a reset jumper in the electronics hardware. At 125, a determination is made as to whether the reset jumper is in place. At 126, the system goes to the RESET subroutine. At 127, the system checks for a display request, i.e., whether the doctor has pushed the button for the display. At 128, a determination is made as to whether the display has been requested. If yes, at 131, the error code is loaded for the error which caused the system to go into the TRMNAT subroutine. At 132, the error code signal is sent to the display for viewing. At 133, a delay is imposed to allow the doctor sufficient time to view the code. At 134, the display subroutine is called to allow the doctor to view the current distraction distance. If no display request has been made, at 129, a delay is imposed to match the time for the error code display and current distraction distance displays. At 129, the "alarm off" delay count is decremented, and at 130, a determination is made as to whether the end of the "alarm off" period is present based on the number loaded at step 121.

Steps 190-225 represent a more detailed or alternative version of the EPROM program. At 190, an initial power-up check is made to be certain that the chip is acceptable, and the RAM is checked. Also, a check is made to be certain that the correct chip has been inserted. At 191, a determination is made as to whether the initial power-up check indicates the system has checked out acceptably. If not, the microprocessor error code is set at 193, and at 194, the system goes to the TRMNAT subroutine. If the system is checking out acceptably, at 192, the WMSTART subroutine from the RESET subroutine is carried out. At 195, a successful power-up code is loaded. At 196, the SYSOK subroutine is called, which will provide an audio OK signal and display a successful power-up code. At 197, the system checks for a start signal (which is a hardware jumper). At 198, the system queries whether a start signal is present. At 199, the CPU clock is synchronized with an external clock to verify that the chip is functioning correctly.

At 200, the motor count is loaded, to indicate the number of motors set in the ROMSET program. At 201, motor x is turned on by supplying power to the motor. At 202, the subroutine MTRCHKON is called, which tests whether there is current to the motor and shuts the system down if not. At 203, motor x is turned off. At 204, subroutine MTRCHKOF is called, which tests whether there is no current to the motor and shuts the system down if there is current to the motor.

At 205, the motor count is decremented by 1. At 206, a determination is made as to whether this is the last motor. At 207, a successful start code is loaded. At 208, the SYSOK subroutine is called, and at 209, the first run flag is burned by physically burning a fuse which acknowledges the successful start-up.

At 210, the total cycle count is loaded, which has been established in the ROMSET program and represents the total number of movements of the motor required to achieve the overall desired distraction for the entire treatment procedure. At 211, the motor count is loaded, which is the number of motors established in the ROMSET program. At 212, the number of pulses to be supplied by motor x is loaded; this number is also established in the ROMSET program. At 213, the motor is turned ON and at 214, the ONPLSTST subroutine is called. This latter subroutine checks to be certain there is current to the motor. There is a cumulative error counter which will cause the system to alarm and shut down if there have been too many times when no current is flowing during motor ON time. At 215, the motor is turned OFF. At 216, the OFPLSTST subroutine is called. This checks to be certain there is no current to the motor when the motor is to be OFF. There is a cumulative error counter which will cause the system to alarm and shut down if there have too many times when current is flowing during motor OFF time. At 217, the motor x pulse count is decremented. For example, if a total of 133 pulse were required, the pulse count would be decremented to 132 after the first time through. At 218, the system checks whether the required pulses (e.g., 133) have been sent. If yes, at 219, the motor count is decremented. At 220, a determination is made as to whether this is the last motor. At 221, the cycle count is decremented, and at 222, a determination is made as to whether the total required cycles for the overall treatment have been completed. If yes, at 223, the completion code is set, and the system proceeds to the TRMNAT subroutine. This latter subroutine causes the system to alarm and allows no further movement of the system. It also allows the doctor to view an error code for problems and display cumulative movements of the telescopic rods prior to system shutdown. It also allows the doctor the option of resetting the system after correcting any problem.

At 225, the LTMDLY subroutine is called. This allows the doctor to display cumulative movement of the telescopic rods. The system checks to be certain that the advancement nut has moved an amount equivalent to the amount expected based on the number of pulses sent to the motor within a specified range. This also provides a delay between motor movements.

With respect to the MTRCHKOF (motor check OFF) subroutine, the logic is the same as the OFPLSTST subroutine.

With respect to the MTRCHKON (motor check ON) subroutine, the logic is the same as the OFPLSTST subroutine.

Turning now to the SYSOK subroutine, at 149, the code is sent to the display, and at 150, the alarm interval is loaded to determine how many times the alarm will beep. At 150, the acoustic alarm code (alarm sound code) is loaded. At 152, the alarm is turned ON, and at 153, a delay is imposed to obtain the desired length of time. At 154, the alarm is turned OFF, and at 155, a delay is imposed to provide the desired time duration between beeps. At 156, a check is made as to whether the alarm interval is complete by keeping track of the number of beeps. At 157, a delay is imposed to allow the doctor or a technician sufficient time to review the code.

With respect to the OFPLSTST subroutine, this is the same as the ONPLSTST subroutine, with the exception that the system checks to be certain that current is zero rather than that current flow is sufficient.

If should be noted that the above description and the accompanying drawings are merely illustrative of the application of the principles of the present invention and are not limiting. Numerous other arrangements which embody the principles of the invention and which fall within its spirit and scope may be readily devised by those skilled in the art. Accordingly, the invention is not limited by the foregoing description, but is only limited by the summary or scope of the invention as described in this application.

What is claimed is:

1. An orthopaedic apparatus, comprising:
   a telescoping rod suitable for placement in a bone of a patient, said telescoping rod including means for adjusting its length
   a plurality of fixing means for securing said telescoping rod to the bone in which it is placed;
   automatic drive means for controlling said means for adjusting the length of said telescoping rod, said drive means comprising a motor for causing incremental adjustments of said means for adjusting to adjust the length of said telescoping rod; and
   a controller means for providing pulses to said motor to control the incremental adjustments of said telescoping rod and for storing information regarding the number of stepwise adjustments of said telescoping rod length by said motor.

2. The orthopaedic apparatus of claim 1, wherein said motor is a digital motor.

3. The orthopaedic apparatus of claim 1, further comprising feedback sensor means for sensing the amount of adjustment of said telescoping rod length and providing data representing said sensed amount of adjustment to said controller means.

4. The orthopaedic apparatus of claim 3, wherein said controller further comprises means for comparing said information regarding the instantaneous number of stepwise adjustments with said data representing said sensed amount of adjustment.

5. The orthopaedic apparatus of claim 4, further comprising display means, connected to said controller means, for displaying a representation of said information regarding said instantaneous number of stepwise adjustments of said telescoping rod length.

6. The orthopaedic apparatus of claim 3, wherein said feedback sensor means is an infrared sensor.

7. The orthopaedic apparatus of claim 3, wherein said feedback sensor means is a magnetic reed switch.

8. The orthopaedic apparatus of claim 1, wherein said controller comprises means for providing a test pulse to said motor and for checking whether said motor responds properly to said pulse.

9. The orthopaedic apparatus of claim 1, wherein said apparatus is fully implantable in a patient.

10. An orthopaedic apparatus, comprising:
    a telescoping rod assembly having an adjustable length;
    adjustment means for adjusting said adjustable length of said telescoping rod assembly;
    a plurality of fixing means for attaching said telescoping rod assembly to bone of a patient; and
    an automatic drive means for controlling said adjustment means to adjust the length of said telescoping rod assembly, said drive means including a controller means for controlling adjustments of said adjustment means to adjust said length of said telescoping rod assembly and for storing information regarding the adjustments of said adjustment means.

11. The orthopaedic apparatus of claim 10, wherein said motor is a digital motor.

12. The orthopaedic apparatus of claim 10, further comprising feedback sensor means for sensing the amount of adjustment of said telescoping rod length and providing data representing said sensed amount of adjustment to said controller means.

13. The orthopaedic apparatus of claim 12, wherein said feedback sensor means is an infrared sensor.

14. The orthopaedic apparatus of claim 12, wherein said feedback sensor means is a magnetic reed switch.

15. The orthopaedic apparatus of claim 10, wherein said controller means stores information regarding the instantaneous number of stepwise adjustments of said adjustment means.

16. The orthopaedic apparatus of claim 15, wherein said controller further comprises means for comparing said information regarding the instantaneous number of stepwise adjustments with said data representing said sensed amount of adjustment.

17. The orthopaedic apparatus of claim 16, further comprising display means, connected to said controller means, for displaying a representation of said information regarding said instantaneous number of stepwise adjustments of said telescoping rod length.

18. The orthopaedic apparatus of claim 10, wherein said controller comprises means for providing a test pulse to said motor and for checking whether said motor responds properly to said pulse.

19. The orthopaedic apparatus of claim 10, wherein said apparatus is fully implantable in a patient.

20. A method of controlling an orthopaedic apparatus which comprises a telescoping rod assembly having an adjustable length, an adjustment means for adjusting said adjustable length of said telescoping rod assembly, a plurality of fixing means for attaching said telescoping rod assembly to bone of a patient, said method comprising:

controlling said adjustment means to adjust said adjustable length of said telescoping rod assembly by employing a motor to incrementally adjust said adjustment means to stepwise adjust said length of said telescoping rod assembly and employing a controller means to provide pulses to said motor to control the incremental adjustments of said telescoping rod assembly and to store information regarding the number of stepwise adjustments of said length of said telescoping rod assembly by said motor.

21. The method of claim 20, wherein said motor is a digital motor.

22. The method of claim 20, further comprising sensing the amount of adjustment of said adjustable length of said telescoping rod assembly and providing data representing said sensed amount of adjustment to said controller means, based on a comparison of said information regarding the number of stepwise adjustments with said data representing said sensed amount of adjustment.

23. The method of claim 20, further comprising displaying a representation of said information regarding said number of stepwise adjustments of said adjustable length of said telescoping rod assembly.

24. The method of claim 20, further comprising providing a test pulse to said motor and checking whether said motor responds properly to said pulse.

* * * * *